US008703440B2

(12) United States Patent
Duymelinck et al.

(10) Patent No.: US 8,703,440 B2
(45) Date of Patent: Apr. 22, 2014

(54) METHODS, REAGENTS AND INSTRUMENTATION FOR PREPARING IMPREGNATED TISSUE SAMPLES SUITABLE FOR HISTOPATHOLOGICAL AND MOLECULAR STUDIES

(75) Inventors: Carla Duymelinck, Kruibeke (BE); Mark Kockx, Edegem (BE)

(73) Assignee: Histogenex N.V., Edegem (BE)

( * ) Notice: Subject to any disclaimer, the term of this patent is extended or adjusted under 35 U.S.C. 154(b) by 1267 days.

(21) Appl. No.: 11/997,306

(22) PCT Filed: Jul. 31, 2006

(86) PCT No.: PCT/EP2006/007577
§ 371 (c)(1),
(2), (4) Date: Jun. 3, 2008

(87) PCT Pub. No.: WO2007/014742
PCT Pub. Date: Feb. 8, 2007

(65) Prior Publication Data
US 2008/0274496 A1     Nov. 6, 2008

(30) Foreign Application Priority Data
Jul. 29, 2005  (WO) ................ PCT/EP2005/008253

(51) Int. Cl.
*G01N 1/30*   (2006.01)
(52) U.S. Cl.
USPC ........................................ 435/40.5
(58) Field of Classification Search
USPC ........................................ 435/40.5
See application file for complete search history.

(56) References Cited

U.S. PATENT DOCUMENTS

| | | |
|---|---|---|
| 3,350,220 A | 10/1967 | Isreeli |
| 3,997,656 A | 12/1976 | Wertlake et al. |
| 4,141,312 A | 2/1979 | Louder et al. |
| 4,483,270 A | 11/1984 | Toya et al. |
| 4,857,300 A | 8/1989 | Maksem |
| 4,935,875 A | 6/1990 | Shah et al. |
| 4,960,224 A | 10/1990 | Boenisch |
| 5,023,187 A | 6/1991 | Koebler et al. |
| 5,089,288 A | 2/1992 | Berger |

(Continued)

FOREIGN PATENT DOCUMENTS

| | | |
|---|---|---|
| DE | 102 40 814 | 3/2004 |
| EP | 0 077 477 | 4/1983 |

(Continued)

OTHER PUBLICATIONS

International Search Report dated Nov. 10, 2006.

*Primary Examiner* — Patricia Leith
(74) *Attorney, Agent, or Firm* — Knobbe, Martens, Olson & Bear LLP

(57) ABSTRACT

A process and kit for the production of paraffin sections of biological tissue, especially for molecular pathology studies, is described. In the process, the tissue sample is simultaneously fixed, dehydrated and cleared in a first step, subsequently dehydrated and cleared in a second step and infiltrated with an inert specimen matrix in a third step. The specimen can then be further embedded in a casting supporting matrix according to the standard procedures followed by any local pathology or research laboratory. The method is uncomplicated, requires little hands-on time, is reproducible and is standardized thereby limiting cross-center pre-analytical variance. A bio-indicator system for measuring the degree of crosslinking is also disclosed.

10 Claims, 20 Drawing Sheets

(56) References Cited

U.S. PATENT DOCUMENTS

| | | | |
|---|---|---|---|
| 5,104,464 A * | 4/1992 | Hasegawa | 148/300 |
| 5,104,640 A | 4/1992 | Stokes | |
| 5,354,370 A | 10/1994 | Schmehl | |
| 5,424,040 A | 6/1995 | Bjornsson | |
| 5,482,591 A | 1/1996 | Reo | |
| 5,817,032 A | 10/1998 | Williamson et al. | |
| 5,869,689 A | 2/1999 | Zhang et al. | |
| 6,026,174 A | 2/2000 | Palcic et al. | |
| 2001/0043884 A1 | 11/2001 | Essenfeld et al. | |
| 2002/0018733 A1 | 2/2002 | Kapplein et al. | |
| 2002/0030598 A1 | 3/2002 | Dombrowski et al. | |
| 2002/0131896 A1 | 9/2002 | Hunnell et al. | |
| 2002/0177183 A1 | 11/2002 | Giberson et al. | |
| 2004/0253662 A1 | 12/2004 | Heid et al. | |
| 2005/0145048 A1 | 7/2005 | Moir et al. | |
| 2008/0103114 A1 * | 5/2008 | Zeligs | 514/80 |
| 2008/0206807 A1 | 8/2008 | Duymelinck et al. | |

FOREIGN PATENT DOCUMENTS

| | | | |
|---|---|---|---|
| EP | 1 130 377 | | 9/2001 |
| EP | 1 455 174 | | 9/2004 |
| GB | 2 379 739 | | 3/2003 |
| WO | WO 99/09390 | * | 2/1999 |
| WO | WO 01/44783 | | 6/2001 |
| WO | WO 01/44784 | | 6/2001 |
| WO | WO 03/029845 | | 4/2003 |
| WO | WO 03/031064 | | 4/2003 |
| WO | WO 03/040697 | | 5/2003 |

* cited by examiner

METHODS, REAGENTS AND INSTRUMENTATION FOR PREPARING IMPREGNATED TISSUE SAMPLES SUITABLE FOR HISTOPATHOLOGICAL AND MOLECULAR STUDIES

CROSS-REFERENCE TO RELATED APPLICATIONS

This application is the U.S. National Phase under 35 U.S.C. §371 of International Application PCT/EP2006/007577, filed Jul. 31, 2006, which claims priority to PCT/EP2005/008253, filed Jul. 29, 2005.

BACKGROUND OF THE INVENTION

Many researchers experience a trade-off between maintaining cell morphology and preserving gene expression information in the same tissue sample. Paraffin-embedded tissue samples generally show good morphology but gene expression data are severely compromised. Conversely, frozen tissue samples remain the gold standard for obtaining high quality gene expression information, but tissue morphology from frozen material is inferior compared to the morphology of paraffin-embedded tissue samples. Given the empirical foundation of microscopic analysis for current methods of tissue diagnosis and prognosis, the transfer of molecular methods into pathology practice has been greatly hampered. Indeed, the development of improved methods for tissue processing for transcript profiling of pathological samples are still necessary (Perlmutter M A, Best C J, Gillespie J W, Gathright Y, Gonzalez S, Velsaco A, Linehand W M, Emmert-Buck M R, Chuaqui R F: Comparison of snap freezing versus ethanol fixation for gene expression profiling of tissue specimens. J Mol Diagn 6(4):371-7, 2004). For gene expression analysis, the presence of intact and extractable nucleic acids from the test material is mandatory. Because the emerging role of transcript profiling studies in research and clinical work, a nucleic acid-friendly fixative with the morphological detail of formalin-fixed paraffin-embedded (FFPE) tissues should replace formalin as the primary (human) tissue fixative.

The cellular abundance of a particular RNA transcript is tightly regulated by the balance between its transcription and degradation rate. It is important for gene expression studies that the measured RNA population reflects the actual transcriptosome present at the time of tissue or cell collection as closely as possible. As RNA is rapidly degraded by ribonucleases, it is of paramount importance to reduce or halt endogenous enzyme activity as quickly as possible prior to or at the time of tissue or cell collection. One way of accomplishing this 'status quo' situation is by freezing techniques such as snap-freezing in liquid nitrogen. However, as known by those persons skilled in the art, the freezing process results in sub-optimal microscopical detail of tissue architecture and cell morphology. Moreover transport of frozen tissues requires specialist shipment and is more costly and risky (chance of defrosting) than transporting paraffin-embedded material. For example, if gene expression studies are performed in a central reference laboratory, e.g. in clinical trials, frozen samples have to be properly prepared for courier shipment. Sometimes, international sample carriage is not possible.

Another problem in the art is the limited tissue biopsy availability. A single small-sized biopsy (e.g. needle biopsy) may not provide sufficient tissue for both classical histopathological analyses and molecular pathology assays. Consequently, it may be required to collect two tissue samples which causes additional distress and injury to the patient.

The extraction of high molecular weight DNA from paraffin-embedded tissue has been reported (e.g. Dubeau L, Chandler L A, Gralow J R, Nichols P W, Jones P A: Southern blot analysis of DNA extracted from formalin-fixed pathology specimens. Cancer Res 1986, 46:2964-2969; Greer C E, Peterson S L, Kiviat N B, Manos M M: PCR amplification from paraffin-embedded tissues. Effects of fixative and fixation time. Am J Clin Pathol 1991, 95:117-124; Inoue T, Nabeshima K, Kataoka H, Koono M: Feasibility of archival non-buffered formalin-fixed and paraffin-embedded tissues for PCR amplification: an analysis of resected gastric carcinoma. Pathol Int 1996, 46:997-1004; Ren Z P, Sällström J, Sundström C, Nistér M, Olsson Y: Recovering DNA and optimizing PCR conditions from microdissected formalin-fixed and paraffin-embedded materials. Pathobiology 2000, 68:215-217). However, prolonged exposure of tissues to the fixative formaldehyde results in irreversible cross-linking of proteins and nucleic acids, causing the maximum PCR amplicon size to be limited (Finkelstein S D, Sayegh R, Christensen S, Swalsky P A: Genotypic classification of colorectal adenocarcinoma. Cancer 1993, 71: 3827-3838). In addition extensive fixation in formaldehyde leads to nucleic acid scission, further diminishing the efficiency of PCR-based analysis and amplicon size. Although DNA survives fixation and embedding reasonably well, RNA content is seriously decreased due to the combination of the presence of RNase activity in virtually all tissues and the use of excessive heating during the infiltration and embedding procedures of the tissue processing. Indeed, it is more difficult to obtain high molecular weight RNA from (archival) paraffin-embedded material. Extraction of RNA with a maximal length of 600 base pairs has been described (Stanta G, Schneider C: RNA extracted from paraffin-embedded human tissues is amenable to analysis by PCR amplification. Biotechniques 1991, 11:304, 306, 308; Krafft A E, Duncan B W, Bijwaard K E, Taubenberger J K, Lichy J H: Optimization of the Isolation and Amplification of RNA From Formalin-fixed, Paraffin-embedded Tissue: The Armed Forces Institute of Pathology Experience and Literature Review. Mol Diagn 1997, 2:217-230; Goldsworthy S M, Stockton P S, Trempus C S, Foley J F, Maronpot R R: Effects of fixation on RNA extraction and amplification from laser capture microdissected tissue. Mol Carcinog 1999, 25:86-91; Specht K, Richter T, Müller U, Walch A, Höfler M W: Quantitative gene expression analysis in microdissected archival tissue by real-time RT-PCR. J Mol Med 2000, 78:B27; Specht K, Richter T, Muller U, Walch A, Werner M, Hofler H: Quantitative gene expression analysis in microdissected archival formalin-fixed and paraffin-embedded tumor tissue. Am J Pathol 2001, 158:419-429; Paska C, Bogi K, Szilak L, Tokes A, Szabo E, Sziller I, Rigo J Jr, Sobel G, Szabo I, Kaposi-Novak P, Kiss A, Schaff Z: Effect of formaline, acetone, and RNAlater fixatives on tissue preservation and different size amplicons by real-time PCR from paraffin-embedded tissue. Diagn Mol Pathol 2004, 13:234-240)

However, such RNA fragment sizes severely limit the suitability of the RNA for certain molecular profiling applications such as the construction of full length cDNA libraries. Even if the average RNA fragment size would be sufficiently large to allow paraffin-embedded tissues or cells to be used for RT-PCR, nucleic acid amplification procedures and microarray analyses, the reliability and reproducibility of quantitative gene expression studies are questionable in the presence of degraded and chemically modified RNA, especially since the different mRNA species from the mRNA pool are most likely not affected to the same degree/extent.

A number of fixative formulations have been described in the art. U.S. Pat. No. 6,319,683 is based on controlling the reactivity of the fixating components by quenching the excess formaldehyde with a formaldehyde reactive agent. U.S. Pat. No. 5,976,829 describes a fixative comprising aldehyde, alcohol and CDTA. WO 03/029783 describes the protection of the tissue specimen by impregnation with an osmotically buffered amino acid solution prior to fixation with an acetone-based fixative, which would obviate the need for a crosslinking agent. WO 00/06780 discloses a method for maintaining RNA integrity in biological materials by means of an RNA preservation medium. Although the patented medium does keep the RNA intact (Mutter G L, Zahrieh D, Liu C, Neuberg D, Finkelstein D, Baker H E, Warrington J A: Comparison of frozen and RNALater solid tissue storage methods for use in RNA expression arrays. *BMC Genomics* 2004, 5:88), in histological applications a variable outcome on tissue morphology and immunostaining has been observed (Florell S R, Coffin C M, Holden J A, Zimmermann J W, Gerwels J W, Summers B K, Jones D A, Leachman S A: Preservation of RNA for functional genomic studies: a multidisciplinary tumor bank protocol. *Mod Pathol* 2001, 14:116-128; Roos-van Groningen M C, Eikmans M, Baelde H J, de Heer H J, Bruijn J A: Improvement of extraction and processing of RNA from renal biopsies. *Kidney Int* 2004, 65:97-105).

U.S. Pat. No. 6,379,921 described a method using a procedure based on a zinc-containing aqueous fixative, an acetone-based clearing agent and molten resin. However, the resulting tissue blocks must be sectioned and processed differently from routine paraffin blocks which may complicate the work-flow in a routine pathology lab.

For future tissue conservation of pathology specimens, it would be desirable to satisfy both histological and molecular biological needs. An uncomplicated fixation and paraffin embedding method that results in tissue sections with the same morphological characteristics as formalin-fixed paraffin-embedded (FFPE) tissues, while preserving nucleic acid integrity would have an important impact on the feasibility and logistics of clinical trials. In addition, such method would greatly facilitate the introduction of gene expression analyses in routine pathology laboratories, especially if it requires no or only limited modification of standard routine downstream pathology protocols.

SUMMARY OF THE INVENTION

One embodiment of the present invention is a method for preparing a tissue sample, suitable for morphological and/or immunohistochemical analysis, and quantitative nucleic acid analysis molecular analysis comprising the steps of:
1) simultaneous fixation, dehydration and initial clearing of the sample using a fixation-dehydration-clearing, FDC, solution, that comprises a cross-linker and an excess of aliphatic or aromatic organic solvent,
2) dehydration and final clearing of the sample using a dehydrating-clearing solution, and
3) infiltrating the sample with an inert specimen matrix, ISM.

One embodiment of the present invention is a method as described above, wherein said FDC solution further comprises a hydrophobic solvent and a pH modifying substance.

One embodiment of the present invention is a method as described above, wherein said cross-linker comprises an aldehyde, preferably at a concentration between 0.2 and 10% (v/v).

One embodiment of the present invention is a method as described above, wherein said FDC solution comprises formaldehyde, methanol, diethylether and/or acetic acid.

One embodiment of the present invention is a method as described above, wherein said FDC solution comprises 0.2 to 10% of formaldehyde, 30 to 90% of methanol, 0 to 25% of diethylether and 0 to 10% of acetic acid.

One embodiment of the present invention is a method as described above, wherein the FDC solution consists of 10% of formaldehyde, 65% of methanol, 20% of diethylether and 5% of acetic acid.

One embodiment of the present invention is a method as described above, wherein said organic solvent is methanol.

One embodiment of the present invention is a method as described above, wherein said pH modifying substance is a weak acid.

One embodiment of the present invention is a method as described above, wherein said pH modifying substance is at a concentration between 0.1% and 10% (v/v).

One embodiment of the present invention is a method as described above, wherein said pH modifying substance is acetic acid.

One embodiment of the present invention is a method as described above, wherein said hydrophobic solvent is diethylether.

One embodiment of the present invention is a method as described above, wherein said hydrophobic solvent is at a concentration between 5% and 25% (v/v).

One embodiment of the present invention is a method as described above, wherein said dehydration-clearing solution comprises one or more of diethylether, dioxane or dimethoxypropane.

One embodiment of the present invention is a method as described above, wherein said ISM is low melting point paraffin.

One embodiment of the present invention is a method as described above, wherein said paraffin infiltrates the sample at a temperature between 45 and 56 deg C.

One embodiment of the present invention is a method as described above, wherein step 1) further comprising the use of a crosslinking indicator to indicate the degree of fixation.

Another embodiment of the present invention is a kit comprising
a) an FDC solution consisting of a cross-linker and an excess of aliphatic or aromatic organic solvent,
b) a dehydrating-clearing solution,
c) an inert specimen matrix, ISM, for infiltrating the tissue samples,
each in separate containers for separate and/or sequential application to the sample.

Another embodiment of the present invention is a kit as described above, wherein said FDC solution has one or more of the features as defined above.

Another embodiment of the present invention is a kit as described above, wherein said dehydrating-clearing solution is as defined above.

Another embodiment of the present invention is a kit as described above, wherein said ISM is low-melting paraffin suitable for impregnating the tissue at a temperature between 45 and 56 deg C.

Another embodiment of the present invention is a kit as described above, further comprising a crosslinking indicator system to indicate the degree of fixation.

Another embodiment of the present invention is an instrument for automation of the method as defined above.

Another embodiment of the present invention is an instrument as defined above comprising one or more of sample receiving means, means for dispensing FDC solution, means for dispensing dehydration-clearing solution, means for dispensing ISM to the sample, means for agitation and means for draining waste solution.

Another embodiment of the present invention is a tissue sample obtainable by to the method as defined above.

Another embodiment of the present invention is a use of an FDC solution as defined above for the preparation of a sample suitable for morphological and/or immunohistochemical, and molecular analysis.

Another embodiment of the present invention is data obtainable by using a paraffin-embedded sample that has been produced according to the method of the present invention.

Another embodiment of the present invention is data as described above, which is one or more of micrograph 2D or 3D (virtual) images of sections, morphological analysis data, nucleic acid concentration and integrity data and data from downstream nucleic acid analyses.

Another embodiment of the present invention is a processing station for preparing a tissue sample suitable for morphological and/or immunohistochemical, and molecular analysis, comprising:
  means (81) to receive a vial (84) of solution for fixation,
  means (82) to receive a vial (85) of solution for clearing,
  means (83) to receive a vial (86) of ISM,
said processing station configured to bring the sample (87) into contact sequentially with the contents of each vial, wherein the means (83) to receive a vial (86) of ISM is disposed with a means for regulating the temperature of said ISM vial.

Another embodiment of the present invention is a processing station as described above, wherein said means (81) to receive a vial (84) of solution for performing fixation is disposed with a means for regulating the temperature of said fixation solution vial (84).

Another embodiment of the present invention is a processing station as described above, wherein at least one vial receiving means comprise fluid and optionally air access means.

Another embodiment of the present invention is a processing station as described above, wherein the respective vial receiving means are arranged as a vertical column.

Another embodiment of the present invention is a processing station as described above, wherein
  said means (81) to receive a vial (84) of fixation solution is positioned towards the centre of the column,
  said means (82) to receive a vial (85) of solution for clearing is positioned towards the top of the column, and
  said means (83) to receive a vial (86) of ISM is positioned towards the base of the column.

Another embodiment of the present invention is a processing station as described above, wherein said means (83) to receive a vial (86) of ISM comprises a vertically moving platform (121).

Another embodiment of the present invention is a processing station as described above, configured to process a sample held in the vial (84) of solution for fixation.

Another embodiment of the present invention is a vial (84) for use in the automated preparation of a tissue sample suitable for morphological and/or immunohistochemical, and molecular analysis, comprising a sample holding means (102) which is configured to immerse the sample in fluid held by the vial.

Another embodiment of the present invention is a vial (84) as described above, comprising at least one breakable seal towards the top of the vial, suitable for receiving or removing fluid therethrough.

Another embodiment of the present invention is a vial (84) as described above, comprising at least one breakable seal towards the top of the vial, suitable for applying positive or negative air pressure to the vial therethrough.

Another embodiment of the present invention is a vial (84) as described above, comprising at least one breakable seal towards the base of the vial, suitable for receiving fluid therethrough.

Another embodiment of the present invention is a kit comprising a vial as defined above, where said vial contains FDC solution as defined above.

Another embodiment of the present invention is a as defined above, further comprising a vial of dehydrating-clearing solution as defined above.

Another embodiment of the present invention is a kit as defined above, further comprising a vial of ISM.

Another embodiment of the present invention is a method for preparing a tissue sample for morphological and/or immunohistochemical analysis, and molecular analysis comprising the steps of:
  1) simultaneous fixation, dehydration and initial clearing of the sample using a fixation-dehydration-clearing, FDC, solution, that comprises
    a cross-linker,
    an excess of aliphatic or aromatic organic solvent, and
    an ether
  2) dehydration and final clearing of the sample using a dehydrating-clearing solution, and
  3) infiltrating the sample with an inert specimen matrix, ISM.

Another embodiment of the present invention is a method as described above, wherein said cross-linker comprises an aldehyde, preferably at a concentration between 0.2% and 10% (v/v).

Another embodiment of the present invention is a method as described above, wherein said organic solvent is methanol.

Another embodiment of the present invention is a method as described above, wherein said ether is at a concentration between 5% and 25% (v/v).

Another embodiment of the present invention is a method as described above, wherein said ether is one that can bind between 0.5 to 7 g water/100 g ether at 20 deg C., and can dissolve between 10 to 60 g paraffin/100 g ether at 20 deg C., Another embodiment of the present invention is a method as described above, wherein said ether is a monoether, a straight or branched ether, an alkyl ether, an alkenyl ether, a $C_2$ to $C_6$ ether, a cyclic ether or a $C_3$ to $C_5$ cyclic ether.

Another embodiment of the present invention is a method as described above, wherein said ether is any of diethyl ether, methyl tertiary butyl ether, dihydrofuran or tetrahydrofuran.

Another embodiment of the present invention is a method as described above, wherein said FDC solution further comprises a pH modifying substance.

Another embodiment of the present invention is a method as described above, wherein said pH modifying substance is a weak acid.

Another embodiment of the present invention is a method as described above, wherein said pH modifying substance is at a concentration between 0.1% and 10% (v/v).

Another embodiment of the present invention is a method as described above, wherein said pH modifying substance is acetic acid.

Another embodiment of the present invention is a method as described above, wherein said FDC solution further comprises formaldehyde, methanol and optionally acetic acid.

Another embodiment of the present invention is a method as described above, wherein said FDC solution comprises 0.2 to 10% formaldehyde, 30 to 90% methanol, 5 to 25% diethylether and 0 to 10% acetic acid (v/v).

Another embodiment of the present invention is a method as described above, wherein the FDC solution consists of 10% formaldehyde, 65% methanol, 20% diethylether and 5% acetic acid (v/v).

Another embodiment of the present invention is a method as described above, wherein said dehydration-clearing solution can bind between 0.5 to 7 g water/100 g solution, and can dissolve between 10 to 60 g paraffin/100 g solution.

Another embodiment of the present invention is a method as described above, wherein dehydration-clearing solution comprises an ether.

Another embodiment of the present invention is a method as described above, wherein said ether is any can bind between 0.5 to 7 g water/100 g ether at 20 deg C., and can dissolve between 10 to 60 g paraffin/100 g ether at 20 deg C.

Another embodiment of the present invention is a method as described above, wherein said ether is a monoether, a straight or branched ether, alkyl, an alkenyl ether, a $C_2$ to $C_6$ ether, a cyclic ether or a $C_3$ to $C_5$ cyclic ether.

Another embodiment of the present invention is a method as described above, wherein said dehydration-clearing solution comprises one or more of diethylether, methyl tertiary butyl ether, hydrofuran, tetrahydrofuran, dioxane or dimethoxypropane.

Another embodiment of the present invention is a method as described above, wherein said ISM is low melting point paraffin.

Another embodiment of the present invention is a method as described above, wherein said paraffin infiltrates the sample at a temperature between 45 and 56 deg C.

Another embodiment of the present invention is a method as described above, wherein step 1) further comprising the use of a crosslinking indicator to indicate the degree of fixation.

Another embodiment of the present invention is a kit comprising:
a) an FDC solution comprising:
  a cross-linker,
  an excess of aliphatic or aromatic organic solvent, and
  an ether Another embodiment of the present invention is a kit according as described above, further comprising
b) a dehydrating-clearing solution.

Another embodiment of the present invention is a kit according as described above, further comprising
c) an inert specimen matrix, ISM, for infiltrating the tissue samples.

Another embodiment of the present invention is a kit according as described above, wherein a), b) and c) are each in separate containers for separate and/or sequential application to the sample.

Another embodiment of the present invention is a kit according as described above, wherein said FDC solution is as defined above.

Another embodiment of the present invention is a kit according as described above, wherein said dehydrating-clearing solution is as defined above.

Another embodiment of the present invention is a kit according as described above, wherein said ISM is low-melting paraffin suitable for impregnating the tissue at a temperature between 45 and 56 deg C.

Another embodiment of the present invention is a kit according as described above, further comprising a crosslinking indicator system to indicate the degree of fixation.

Another embodiment of the present invention is a tissue sample obtainable by to the method as described above.

Another embodiment of the present invention is a use of an FDC solution as defined above for the preparation of a sample suitable for morphological and/or immunohistochemical, and molecular analysis.

Another embodiment of the present invention is data obtainable by using a paraffin-embedded sample that has been produced according to the method of the present invention.

Another embodiment of the present invention is data as described above, which is one or more of micrograph 2D or 3D (virtual) images of sections, morphological analysis data, nucleic acid concentration and integrity data and data from downstream nucleic acid analyses.

DETAILED DESCRIPTION OF THE PRESENT INVENTION

Figure 1:
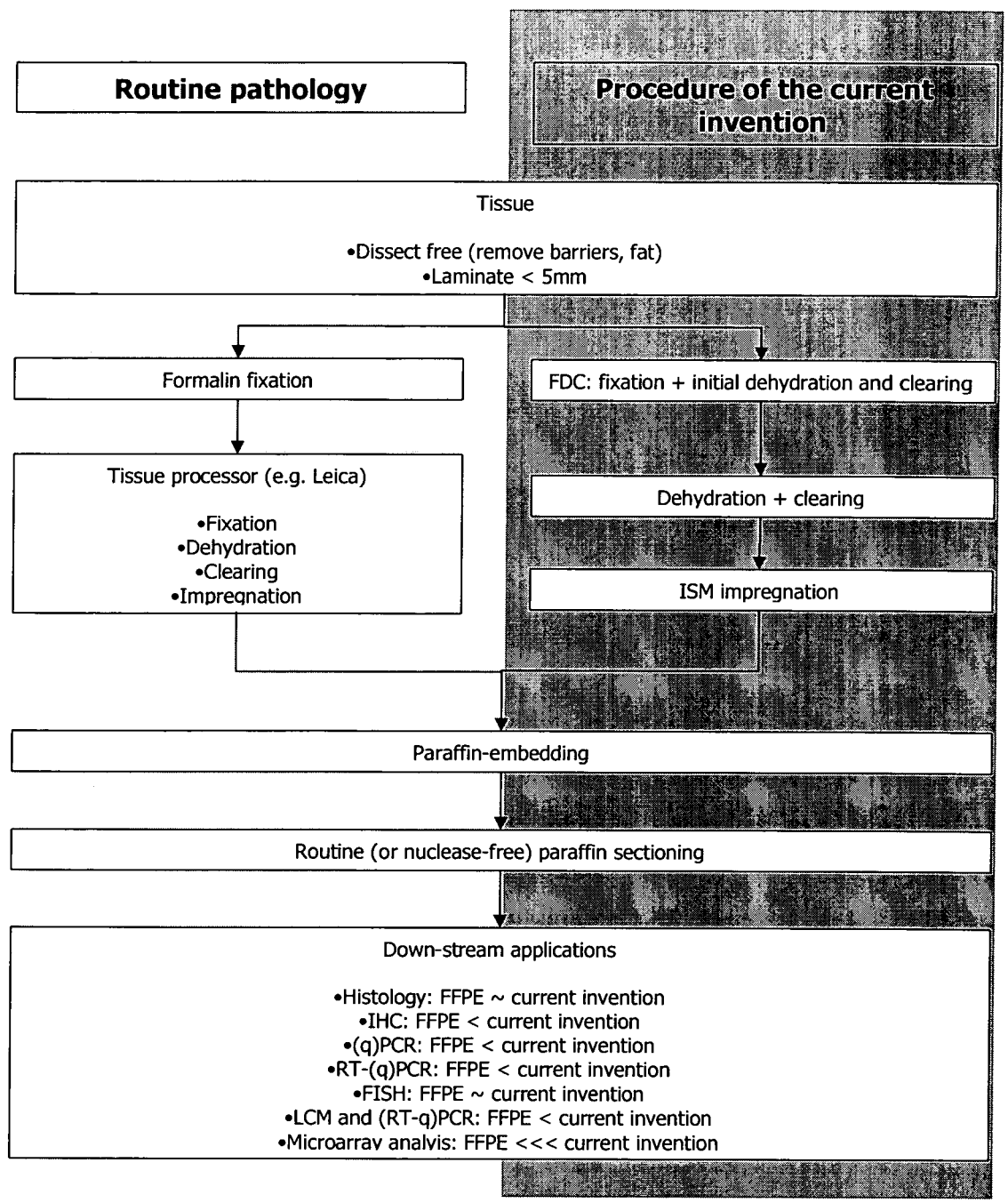
FIG. 1 is a flow chart showing an exemplary general manner of tissue processing as it is performed in a routine pathology laboratory. It further shows how the present invention can be uncoupled from and subsequently brought back into the routine pathology laboratory work-flow.

The present invention is concerned with a sample processing method for the production of sections that are suitable for morphological and/or immunohistochemical analyses, and for molecular analysis (e.g. nucleic acid analysis, quantitative nucleic analysis, qualitative nucleic acid analysis etc), by following certain consecutive processes:
1) simultaneous fixation, dehydration and initial clearing of the sample using a combined fixation-dehydration-clearing solution, called FDC solution hereafter,
2) combined dehydration and final clearing using a dehydration-clearing solution, and
3) impregnation of the sample with an inert specimen matrix (ISM).

Samples processed as described in the present invention can be subsequently paraffin embedded according to local procedures applied in any routine pathology or research laboratory. The resulting paraffin embedded tissue blocks can be sectioned at room temperature.

The present invention also relates to an instrument and processing station for automation of the 3-steps procedure. It also relates to a kit of reagents for implementing the sample processing method according to the invention.

The articles "a" and "an" are used in this document to refer to "one" or to "more than one", for example, "a sample" means "one sample or more than one sample".

All ranges are inclusive. For example, a concentration between 3.0 and 6.0 g/ml includes 3.0 and 6.0 g/ml.

Unless otherwise stated, all percentage amounts are v/v.

Within the scope of the present invention, a sample refers to a biological specimen undergoing preservation. The sample may be either a cell, a part of a tissue, part of an organ, part of a tumour, or combination of such components. The sample may be human in origin, or derived from mouse, rabbit, human, goat, mouse, rat, cow, calf, camel, llama, monkey, donkey, guinea pig, pig, chicken or sheep, or any other vertebrate, invertebrate or plant.

We present an invention that allows a controlled sample fixation/dehydration/clearing and impregnation with an ISM that can be fully standardized by using a maximum of three components (FDC solution, dehydration-clearing solution and ISM). The additional strength of the present invention is that each sample is processed in fresh uncontaminated reagents which enables maximal control of the specimen processing steps and a decrease of cross-centre sample processing variation during the pre-analytical phase.

Step 1: The combined fixation-dehydration-clearing (FDC) step of the present invention rapidly preserves the cellular morphology while retaining the immunohistological profile intact and keeping the chemical modification of the nucleic acids to a limit. In addition to fixation, it simultaneously dehydrates and partially clears the sample. According to the present invention, the sample is incubated in a fixation-dehydration-clearing (FDC) solution comprising of a cross-linker, an excess of organic solvent and an acid.

The cross-linker may be any known in the art. Preferably it comprises an aldehyde. Preferably it comprises a formaldehyde. Formaldehyde used in the present invention is saturated aqueous formaldehyde which is known as a 100% saturated, 37% w/w, 40% w/v or a 13.3M solution. The quantity of formaldehyde in the present invention is expressed as the quantity of formaldehyde and not of the saturated aqueous formaldehyde. The quantity of cross-linking aldehyde present in the FDC solution is less than or equal to 13, 12, 11, 10, 9, 8, 7, 6, 5, 4, 3, 2, 1, 0.5, 0.2% (v/v), or a quantity between any two of the aforementioned values. Preferably, the quantity of cross-linking aldehyde is between 0.2 to 10% (v/v). Most preferably the percentage (v/v) of formaldehyde solution is 10%.

The organic solvent can either be an aliphatic or aromatic solvent. Preferably, the organic solvent is a mono- or polyalcohol, or a mixture thereof in any given ratio. Most preferably, the organic solvent is methanol. The quantity of organic solvent present in the FDC solution is less than or equal to 95, 90, 85, 80, 75, 70, 65, 60, 55, 50, 45, 40, 35, 30, 25, 20, 15% (v/v), or a quantity between any two of the aforementioned values. Preferably, the quantity of organic solvent is between 30 and 90% (v/v). Most preferably the methanol percentage is 65% (v/v).

The FDC solution may further comprise an acid that counteracts the methanol-induced shrinkage of the cellular tissue components. In addition, the pH decrease caused by the addition of an acid increases the reactivity of formaldehyde by the formation of a carbonyl ion that results in faster fixation through reacting with alkenes and N, S and O ions. The acid may be a weak acid. The weak acid is added until the pH of the FDC solution is less than or equal to pH 7.0, 6.5, 6.0, 5.5, 5.0, 4.5, 4.0, 3.5, 3.0, 2.5, 2.0 or a value between any two of the aforementioned values, and is between preferably 2.0 to 7.0. Most preferably, the pH of the FDC solution is between 3.0 and 6.0. Alternatively, the quantity of weak acid present in the FDC solution may be less than or equal to 15, 14, 13, 12, 11, 10, 9, 8, 7, 6, 5, 4, 3, 2, 1, 0.5, 0.2%, 0.1% (v/v) or a quantity between any two of the aforementioned values. The weak acid is preferably acetic acid. The quantity of acetic acid is preferably between 0.1% and 10% (v/v), and most preferably 5% (v/v).

The FDC solution may further comprise a hydrophobic solvent which is soluble in the fixative solution. This solvent increases infiltration and dehydrates the specimen, thus preparing the sample for the actual dehydration-clearing step.

According to one aspect of the invention, the hydrophobic solvent is an ether. An ether has a chemical characteristic defined as having an oxygen atom bonded to two carbon atoms i.e. C—O—C. Ethers have the property that they can both bind a limited amount of water and can dissolve paraffin, according to experiments performed by the inventors. It thus appears to have the appropriate polar and apolar characteristics.

Most existing histological solvents (e.g. Toluol, Xylene, Chloroform) only dissolve paraffin or fail to dissolve paraffin (methanol, isopropanol, ethanol, propanol, ketones and glycols). The inventors have found that ethers are ideally suited in the presently claimed method.

According to one aspect of the invention, an ether is able to bind more than or equal to 0.5, 1, 2, 3, 4, 5, 6, 7, 8, 9 or 10 g water/100 g ether at 20 deg C., or an amount in the range between any two of the aforementioned values. Preferable, an ether is able to bind between 0.5 and 7 g water/100 g ether at 20 deg C.

According to another aspect of the invention, an ether is also able to dissolve more than or equal to 1, 2, 3, 4, 5, 6, 7, 8, 9, 10, 15, 20, 25, 30, 35, 40, 45, 50, 55, 60, 65, 70 g paraffin/100 g ether at 20 deg C., or an amount in the range between any two of the aforementioned values. Preferable, an ether is able to dissolve between 10 and 60 g paraffin/100 g ether at 20 deg C.

Preferably an ether is able to bind water (0.5 to 5 gram/100 gram at 20 deg C.) and can dissolve paraffin (15 to 50 gram/100 gram at 20 deg C.).

Said ether may be a monoether, having one oxygen atom surrounded by 2 carbon atoms). Said ether may be a straight or branched ether. It may be an alkyl or an alkenyl ether. The ether may be a $C_2$ to $C_6$ ether. The may be a cyclic ether. It may be a $C_3$ to $C_5$ cyclic ether.

According to one aspect of the invention, the ether comprises diethyl ether. According to another aspect of the invention, the ether comprises methyl tertiary butyl ether (MTBE). According to another aspect of the invention, the ether comprises dihydrofuran. According to another aspect of the invention, the ether comprises tetrahydrofuran.

The quantity of hydrophobic solvent present in the FDC solution may be less than or equal to 1.0, 2.0, 3.0, 4.0, 5.0, 6.0, 7.0, 8.0, 9.0, 10.0, 12.0, 14.0, 16.0, 18.0, 20.0, 22.0, 24.0, 26.0, 28.0, 30.0% (v/v), or a value between any two of the aforementioned values. Preferably, the solvent percentage lies between 15.0 and 25.0% (v/v). Most preferably the solvent percentage is 20%.

The simultaneous fixation-dehydration-clearing step may be performed by incubating the sample, with or without agitation, for a period of time in the FDC solution.

A typical tissue specimen may be incubated for less than or approximately 3, 6, 9, 12, 14, 16, 18, 20, 22, 24, 26, 28, 30, 32, 34, 36, 40, 44, 48, 52, 55, 60, 65, 70, 75, 80 hours, or for a time between any two of the aforementioned values. Preferably the sample is incubated between 3 and 24 hours.

A typical tissue specimen may be incubated in a volume less than or equal to 10, 20, 30, 40, 50, 60, 70, 80, 90, 100 volume parts of FDC solution per volume part of specimen, or in a volume between any two of the aforementioned values. Preferably the specimen is incubated in between 10 and 50 volume parts of FDC solution per volume part specimen.

Simultaneous to the fixation, the FDC solution also performs the task of dehydrating the sample. In the prior art such procedure is performed after the fixation by consecutive incubations in dehydrating agents. According to the prior art, removal of fixative and water from the tissue and replacing them with dehydrating fluid may take at least three incubations after fixation, increasing the sample manipulation (time) and consequently increasing the risk of inducing more sample damage. The present invention reduces sample manipulation time and the need for additional reagents by using an FDC solution which simultaneously fixes, dehydrates and clears the sample. The sample can be transferred directed to the clearing-dehydration solution in the next step, without the need for a dedicated dehydration step.

Routine pathology labs traditionally use 4% neutral buffered formalin (NBF). NBF is theoretically suited for preserving cell morphology by cross-linking proteins and to a lesser extent, nucleic acids. In reality, NBF also suffers from a number of drawbacks. The rate of fixation by neutral formaldehyde is variable and slow. Furthermore, the cross-linking process results in extensive chemical modifications of the nucleic acids, which inhibit further downstream enzymatic processing of the extracted nucleic acids, e.g. in PCR-based amplification assays.

Step 1 may be performed at a temperature equal to or lower than 5, 10, 15, 20, 25, 30, 35, 40, 45 or 50 deg C., or a value in the range between any two of the aforementioned values. Preferably, step 1 is performed at a temperature between 5 and 45 deg C. Even more preferably it is performed at a temperature between 10 and 35 deg C.

Crosslinking Indicator

Step 1 of the present invention may incorporate a system for indicating the degree of fixation in the sample caused by the cross-linker. The degree indicated by the system may be caused by any type of crosslinker known in the art, such as aldehydes or formaldehyde, and so can be applied to methods besides the method disclosed herein.

According to one aspect of the invention, the crosslinking indicator system comprises the use of at least one crosslinking indicator in which a directly or indirectly measurable property changes proportionally to the activity of the crosslinker or to the degree of crosslinking achieved over time. The measurable property can be any of the art, such as, for example, an observable colour change, a colour change upon further processing, a change in polarisation, change in spectroscopic property, a change in light transmission, a change in light scattering etc. It is an aspect of the invention that said crosslinking indicator is one that can be crosslinked, such as, for example, extracellular matrix components, or collagen.

Said crosslinking indicator may be immobilised on a solid support, such as, for example, nitrocellulose, magnetic beads or any suitable polymeric support. Such crosslinking indicator can be contacted with the crosslinking agent the same time as the sample.

Such a crosslinking indicator system allows the operator of the invention to measure, document and quality control the pre-analytical fixation of any tissue processing method involving any crosslinking agent known to the prior art. This also enables samples processed in different laboratories to be standardised and calibrated.

One embodiment of the present invention is a method of the present invention, wherein step 1 further comprises the step of simultaneously contacting FDC with a crosslinking indicator system. Thus, both sample and a crosslinking indicator system contact the FDC at essentially the same time.

The cross-linking indicator system can be integrated into any process where cross-linking occurs, and needs to be monitored. It may be incorporated into any vial containing crosslinking agent, or be added as a separate unit to a vial containing crosslinking agent, or incorporated into a tissue processing apparatus or technology known to the prior art. The crosslinking indicator system can be incorporated into any method developed to analyse/measure the crosslinker induced (bio)chemical or biological alterations.

Step 2. In this step of the method, the sample is incubated in a dehydration-clearing solution. The dehydration-clearing solution completes the dehydration and clearing of the sample. The dehydration-clearing solution comprises a solvent that is miscible with both water and with the ISM. A purpose of step 2 is to prepare the sample for transition from the hydrophilic fixative to the hydrophobic embedding medium. It facilitates infiltration of the sample with ISM, it removes FDC solution and, thus, diminishes the reactivity of residual formaldehyde with the sample nucleic acids at the elevated temperatures used for impregnation and embedding the sample with ISM. It also acts to remove lipids that may shield specific tissue targets and to permeate plasma membranes.

According to one aspect of the invention, the dehydration-clearing solution is able to bind more than or equal to 0.5, 1, 2, 3, 4, 5, 6, 7, 8, 9 or 10 g water/100 g solution at 20 deg C., or an amount in the range between any two of the aforementioned values. Preferably, the dehydration-clearing solution is able to bind between 0.5 and 7 g water/100 g solution at 20 deg C.

According to another aspect of the invention, the dehydration-clearing solution is also able to dissolve more than or equal to 1, 2, 3, 4, 5, 6, 7, 8, 9, 10, 15, 20, 25, 30, 35, 40, 45, 50, 55, 60, 65, 70 g paraffin/100 g solution at 20 deg C., or an amount in the range between any two of the aforementioned values. Preferably, the dehydration-clearing solution is able to bind between 10 and 60 g paraffin/100 g solution at 20 deg C.

Preferably dehydration-clearing solution is able to bind water (0.5 to 5 gram/100 at 20 deg C.) gram and can dissolve paraffin (15 to 50 gram/100 gram at 20 deg C.).

According to one aspect of the invention, the dehydration-clearing solution comprises an ether. Said ether is able to bind more than or equal to 0.5, 1, 2, 3, 4, 5, 6, 7, 8, 9 or 10 g water/100 g ether at 20 deg C., or an amount in the range between any two of the aforementioned values. Preferably, the ether is able to bind between 0.5 and 7 g water/100 g solution at 20 deg C.

Said ether may be a monoether, having one oxygen atom surrounded by 2 carbon atoms). Said ether may be a straight or branched ether. It may be an alkyl or an alkenyl ether. The ether may be a $C_2$ to $C_6$ ether. The may be a cyclic ether. It may be a $C_3$ to $C_5$ cyclic ether. According to one aspect of the invention, the ether may be one or more of diethyl ether, methyl tertiary butyl ether, dihydrofuran, tetrahydrofuran, dioxane (1,4 diethylene dioxide) or dimethoxypropane (DMP). According to another aspect of the invention, the clearing solution preferably comprises diethylether.

According to one aspect of the invention, the dehydration-clearing solution comprises more than or equal to 10, 15, 20, 25, 30, 35, 40, 45, 50% (v/v) ether, or an amount in the range between any two of the aforementioned values. Preferably, the dehydration-clearing solution comprises 25% or more ether.

Where the dehydration-clearing solution comprises ether, it may also comprise a more apolar solvent. Such solvent may be any of halogenated $C_1$ to $C_6$ alkyls e.g. trichloroethane, halogenated $C_1$ to $C_6$ alkenyl e.g. trichloroethylene.

A typical sample may be incubated in the dehydrating-clearing solution with or without agitation for less than or approximately 1, 2, 3, 4, 5, 6, 8, 9, 10, 10, 12, 14, 16, 18, 20, 24, 28, 32, 36, 40, 44, or 48 hours, or for a time between any two of the aforementioned values. Preferably said sample is incubated between 1 and 24 hours in dehydrating-clearing solution.

A typical sample may be incubated in a volume less than or equal to 10, 20, 30, 40, 50, 60, 70, 80, 90, 100 volume parts of FDC solution per volume part of specimen, or in a volume between any two of the aforementioned values. Preferably the specimen is incubated in 10 to 50 volume parts of FDC solution per volume part specimen. The sample may be transferred to the specimen infiltration matrix without any further treatment.

Step 2 may be performed at a temperature equal to or lower than 5, 10, 15, 20, 25, 30, 35, 40, 45 or 50 deg C., or a value in the range between any two of the aforementioned values. Preferably, step 2 is performed at a temperature between 5 and 45 deg C. Even more preferably it is performed at a temperature between 10 and 35 deg C.

Step 3. In this step of the method, the sample is impregnated with an inert specimen matrix (ISM) that serves to support the specimen and give it sufficient rigidity to enable sections to be cut. The sample is impregnated by the ISM in the liquid form, which solidifies during the embedding. The ISM can be polyester wax, ester wax, carbowax polyethylene glycol, paraffin, a mixture of paraffin with plastic polymers, araldite, aromatic polyepoxide, diethylene glycol distearate, epon, glycol methacrylate, polyethylene glycol-glycol methacrylate, acrylate and polyester resins or Lowicryl. The ISM is preferably hydrophobic. The ISM may solidify at room or at higher or lower temperatures, may be cured by UV irradiation or set after addition of a catalyst. The infiltrating medium may be paraffin. Preferably it is a low-melting paraffin.

Where paraffin is used, it can be any type suitable for infiltrating and embedding samples. Generally, the paraffin is solid at or below room temperature, but melts when heated. According to one aspect of the invention, the ISM used for impregnation is liquid at a temperature less than or equal to 37, 40, 41, 42, 43, 44, 45, 46, 47, 48, 49, 50, 51, 52, 53, 54, 55, 56, 58, 60 to 65 deg C., or a value between any two of the aforementioned values. The ISM is preferably paraffin which melts between 37 and 65 deg C. According to another aspect of the invention, the sample is impregnated with liquid ISM at a temperature between 50 and 60 deg C., and preferably at a temperature higher than or equal to 55 deg C. Unlike methods of the art, in the current invention, a single incubation in the ISM is sufficient. Methods of the art use at least two treatments for prolonged periods and at increased temperatures, which could lead to further nucleic acid degradation and modification.

The temperature at which the sample is impregnated with the ISM can be more important than the embedding temperature, because of the longer duration of sample impregnation. Nucleic acid uncoiling is a temperature-dependent process; in their native states DNA and RNA do not react to any extent with aldehyde cross-linkers. However when samples are heated to about 45 deg C. in the case of RNA and 65 deg C. in the case of DNA, aldehydes may begin to react with the nucleic acids. After uncoiling of DNA and RNA the aldehyde molecules gain access to the reactive moieties of the nucleic acids. Therefore, the infiltration should be performed at between 52 and 58 deg C., for a well defined time interval such as 10, 20, 30, 40, 50, 60, 70, 80, 90, 100, 110, 120, 130, 140, 150, 160, 170, 180, 240 minutes, or for a period in the range between any two of the aforementioned times. Preferably infiltration proceeds for between 60 and 180 minutes.

The impregnation medium and embedding medium may be the same or may differ.

After the sample has been impregnated, it is usually embedded in a suitable substrate according to methods known in the art, such as paraffin. According to an aspect of the invention, paraffin embedding is performed at 40 to 65, 55 to 65, preferably at 60 deg C.

The current invention employs a complete sample fixation and processing system, which comprises three components (FDC solution, dehydration-clearing solution and ISM) that can be fully standardised. The described tissue processing results in tissue ready for standard paraffin-embedding that has good morphological detail and minimally modified nucleic acids. The additional strength of the proposed method is that each sample is separately processed in fresh and uncontaminated solutions which enables maximal control of the tissue processing steps and a decrease of sample processing induced cross-centre variation during the pre-analytical phase. In addition, the method uses less solution types in smaller volumes compared with the prior art, being both ecological and economical.

The combination of different solvents in the FDC solution enhances the tissue infiltration rate and controls the concentration of the monomeric cross-linking aldehyde. This not only optimally preserves the cellular and nuclear morphology and the immunohistochemical profile but also prevents pronounced RNA degradation and modification.

Therefore, the present invention is particularly useful in those applications where excellent tissue morphology and immunohistochemical profile should be combined with downstream applications requiring superior RNA quality such as molecular profiling studies on laser capture microdissected tissue and cells. Furthermore, the expensive and risky storage and transport of frozen tissue specimens is avoided. Both morphological, immunohistochemical and molecular data can be obtained from a single tissue biopsy when the tissue supply is limited.

Kit

A kit according to the present invention allows a skilled artisan to perform one or more steps of the method disclosed herein, in an uncomplicated manner. The kit may allow a method of the present invention to be performed without the need to measure or determine the concentrations of reagents, so enabling a fast and reproducible treatment of one or more samples.

A kit according to the present invention comprises at least one of the components described above for performing a method of the invention on a sample. According to one embodiment, a kit may comprise one or more of an FDC solution as defined above for simultaneous fixation, dehydration and initial clearing of the sample,
a dehydration-clearing solution as defined above and
an ISM for infiltrating samples as defined above, each in separate vials for sequential or stand-alone application to the sample.

The kit may also incorporate the crosslinking indicator system described above. The system may be integrated into the vial containing the FDC solution. In addition, the (bio) indicator system may also be a separate unit that can be added to the first vial of the kit.

The kit may be 'one use only', in which case a single kit is sufficient for the treatment of a single sample. Alternatively, the kit may comprise reagents for the treatment of several samples and may comprise multiple single-use containers. Preferably, the kit is configured in a way that no dilutions, weighing or measurements need to be performed by the user.

A container may be any sealed or resealable vessel suitable for carrying a quantity of reagent. Examples include, but are not limited to screw cap vials, push cap vials, break-seal-to-open vials or syringes.

All kits according to the invention may comprise the stated items or combinations of items and packaging materials therefore. Kits may also include instructions for use.

The kit according to the present invention may comprise as few as three containers, one each for the FDC solution, dehydrating-clearing solution and ISM. In contrast methods of the prior art require several washes with clearing solution, additional solutions for dehydration and two treatments with impregnation sample matrix. A small and straightforward kit is both more economical to manufacture, transport and store, and is easier to use compared with those of the art.

According to one aspect of the invention, a kit comprises a collection of three vials, as described below, respectively containing FDC, dehydration-clearing solution and ISM.

Instrument

Another aspect of the invention is an instrument for automation of the subsequent steps of the present invention. The instrument comprises means for receiving a sample, means for dispensing FDC solution, dehydrating-clearing solution and ISM to the sample, optionally means for agitation and means for draining waste solution. It may also comprise a programming means so the present method can be reproducibly performed in the case of, for example, standarisations or comparative studies. It may also be equipped with temperature control. It may also comprise a system for temperature and/or time registration.

Processing Station

In describing embodiments of a processing station and vials below, reference is made to the drawings in FIGS. 8 to 12. However, the drawings serve only to illustrate the invention, and are not intended in any way limit the invention.

Figure 8:
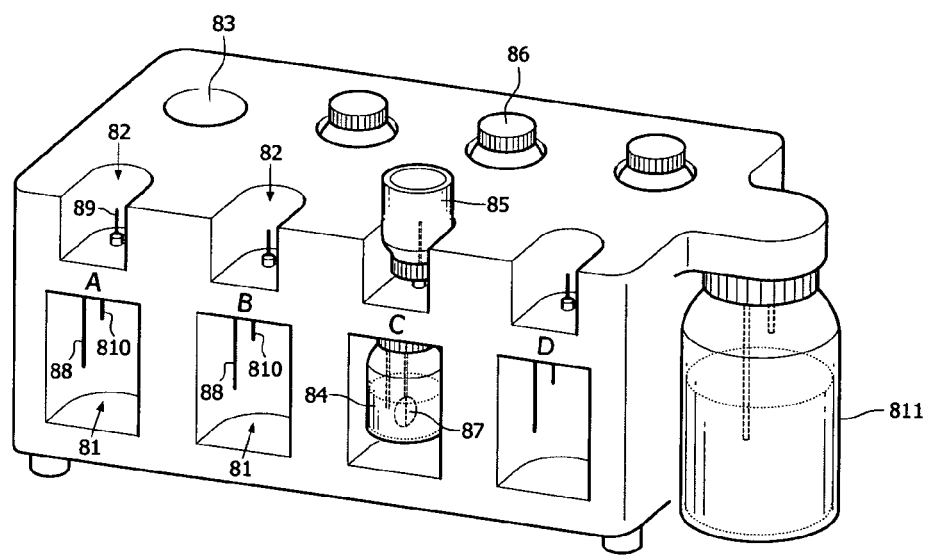
FIG. 8: A machine according to a preferred embodiment of the invention comprising four processing stations for the automated fixing, clearing and impregnation of four samples.

With reference to the drawing in FIG. 8, one aspect of the present invention is a processing station for preparing a paraffin embedded tissue sample suitable for histopathological and molecular analysis, comprising:

means 81 to receive a vial 84 of solution for performing fixation,
means 82 to receive a vial 85 of solution for clearing,
means 83 to receive a vial 86 of substance for inert specimen matrix (ISM), said processing station configured to bring the sample 87 into contact sequentially with the contents of each vial, wherein the means 83 to receive a vial 86 of ISM is disposed with a means for regulating the temperature of said ISM vial. By being able to heat the ISM vial, the ISM can be conveniently provided in a predispensed solid form for transport and storage, and melted and maintained in the molten state during processing. The automation of the device ensures consistent sample processing, critical for comparative studies, especially quantitative measurements. The vials can contain a pre-measured amount of reagent, so alleviating the burden of measuring reagent and reducing measuring errors.

FIG. 8 depicts a processing machine comprising four processing stations of the present invention (A, B, C, D) in a side-by-side configuration. The number of processing stations which can be incorporated into a single device can be one or more than one. Factors which can influence the number of stations in a processing machine include the space available, the specification of shared components (e.g. air and vacuum pumps) to serve a plurality of processing stations, cost etc.

According to a preferred aspect of the present invention a vial of solution for performing fixation contains FDC, a vial of solution for clearing contains dehydration-clearing solution, and a vial of ISM contains low melting point paraffin. Said three vial (step) method is described above.

Means to Receive a Vial

A means to receive a vial (vial receiving means, 81, 82, 83) may comprise at least one fluid access means (88, 89), so the contents of a vial can be accessed and transferring to a desired location. The fluid access means (88, 89) may be a hollow elongate member such as a tube, a needle, a nozzle etc. which preferably engages with a reciprocal feature on the vial, such as an opening, a septum or coupling.

The vial receiving means (81, 82, 83) may also comprise an air access means (810) to supply and extract air to a vial (84, 85, 86), so the contents of a vial can be empted or filled by the application of pressurised air or a vacuum, or which can simply act as an air vent. The air access means (810) may be a hollow elongate member such as a tube, a needle, a nozzle etc. which preferably engages with a reciprocal feature on the vial, such as an opening, a septum or coupling.

The vial receiving means (81, 82, 83) may comprise a cavity with a base for holding the vial, the cavity walls at least partially enclosing the vial. The vial receiving means can be configured according to the action performed on the vial, according to the knowledge of skilled person. For example, where the vial receiving means (83) will hold a vial (86) of ISM in a molten state, the base and walls may be shaped to closely fit the outer shape of the vial. The wall may also be at least partially provided with heating and cooling means (e.g. heating elements, circulating cooling liquid, Peltier device).

In another example, where the contents of a vial are only to be emptied, the vial receiving means may be provided with just the fluid access means (89). Said fluid access means preferably engages with part of a breakable seal (91, 94, FIG. 9) present on the vial (85, 86)

In another example, a vial (84) may be used as the vessel in which the sample (87) is processed, as described below. In such case, during processing, the vial (84) is emptied, and later filled with a different solution; to facilitate emptying and refilling, the vial receiving means (81) may be provided with both the fluid access means (88) and air access means (810). Said fluid and air access means preferably engage with corresponding breakable seals (92, 93, FIG. 9) present on the vial (84).

Where the vial (84) is used as the sample processing vessel, the base and walls of the vial receiving means (81) may be shaped to closely fit the outer shape of the vial and disposed with a means to regulate the temperature of the vial, so that the steps of fixation and clearing, for example, can be performed at a lower temperature than the steps of impregnation, and can be raised during impregnation.

Vials

A vial (84, 85, 86) for use in the processing station preferably contains sufficient solution for a processing step on a single sample. A vial may be made substantially of glass, polycarbonate, polycarbonate or any material of combination of materials compatible with the contents of the vial.

Figure 9:
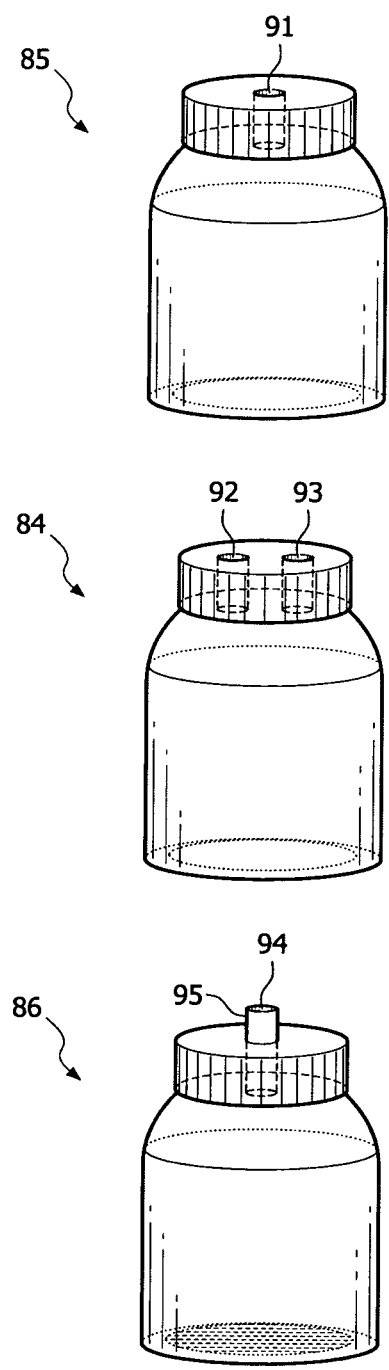
FIG. 9: Three vial according to a preferred embodiment of the invention suitable for use in the machine of FIG. 8 or FIG. 12.

With reference to FIG. 9, a vial for use in the processing station may be sealed with one or more breakable seals (91, 92, 93, 94) so that during storage and transport, the vial is sealed from the air. Prior to use, the seal may be broken by the operator, or a seal breaking means comprised in the vial receiving means. The breakable seal can be any suitable known in the art and can include a septum, a weakened joint which can be broken upon the application of force, a pull strip, a valve, a plug, a sealing bolt, a foil seal etc. A breakable seal can be resealable, or non-resealable. According to one aspect of the invention, the breakable seal is a foil seal breakable by the fluid access means and/or by the air access means. Preferably, a breakable seal is configured to engage with the fluid access means of the vial receiving means, and optionally another breakable seal may engage with the air access means of the vial receiving means. By engaging, a connection is made so that fluid and optionally air can enter and/or leave the vial. Preferably the connection allows air or fluid exchange under pressure or vacuum.

Fixation Vial

Figure 10A:
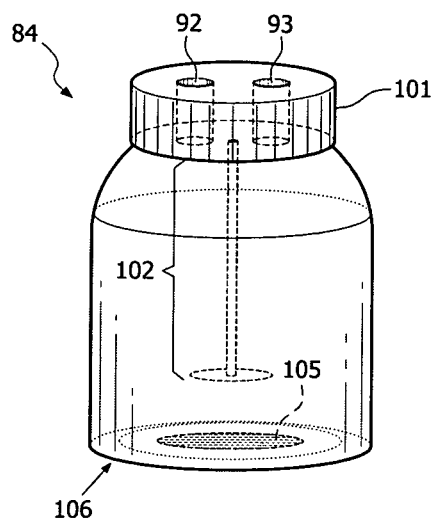
FIG. 10A: Vial according to a preferred embodiment of the invention for combined use as fixative carrier and sample processing vessel, suitable for use in the machine of FIG. 8 or FIG. 12.

With reference to FIG. 10A, another embodiment of the invention, is vial (84) suitable for holding fixation solution (e.g. FDC), comprising a means (102) to hold the sample. The sample holding means (102) is preferably configured to immerse the sample in the solution held by the vial. Such vial (84) can be the container in which the subsequent steps of processing are performed.

The sample holding means (102) can be incorporated into a resealable lid (e.g. screw cap) (101) of the fixation solution vial. Removing the lid (101) allows access to the sample holding means so the sample can be attached before and removed after processing.

Figure 10B:
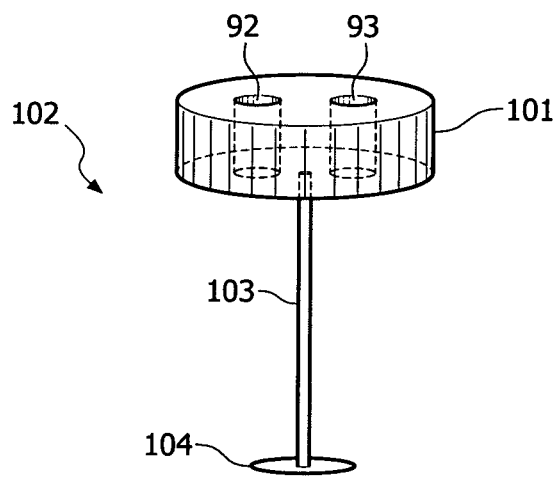
FIG. 10B: Detail of the lid and sample holding means of vial of FIG. 10A.
Figure 11:
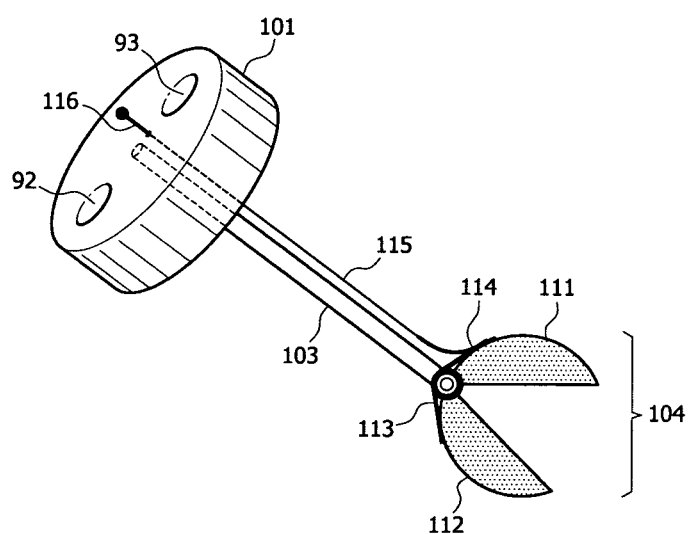
FIG. 11: Detail of according to a preferred embodiment of sample supporting means.

With reference to FIG. 10B, according to one aspect of the invention, the sample holding means comprises an elongate body (103) protruding from the resealable lid (101) of the fixation solution vial (84). The elongate body (103) ends in a means (104) to support the sample. The sample supporting means can be any suitable structure such as a gridded platform provided with a clip to hold the sample on the platform. With reference to FIG. 11, the sample supporting means can comprise a pair of jaws (111, 112) normally held shut by means of a stainless steel spring (113). The jaws can be opened by means of a wire (115) attached (114) to one jaw (111) which leads to an operating means (116) in the lid. Pulling on the wire (115) opens the jaw (111), allowing a sample to be placed between the jaws. Alternatively, the jaws may be configured so pushing on wire in the direction of the sample (115) opens the jaws, said configuration akin to that of a retracting sugar tong.

According to one aspect of the invention, the sample holding means (102) is disposed with a weight sensor for measuring the mass of the sample. The weight sensor can be built into the aforementioned means (104) to support the sample, for example. By measuring the mass of the sample, the times, temperatures and/or volumes of reagent can be adjusted to optimise the processing.

According to another aspect of the invention, the fixation vial receiving means (81) comprises a level sensor, which measures the level of the fixation fluid in the fixation vial. Thus, when a sample is introduced, the volume of fluid displaced by the sample can be determined, and accordingly, the volume of the sample. By measuring the mass of the volume, the times, temperatures and/or volumes of reagent can be adjusted to optimise the processing. In combination with knowledge of the mass of the sample, still more optimised conditions can be employed.

Another embodiment of the present invention is a fixation solution vial (84) as described herein, comprising a breakable seal (105, FIG. 10) for the entry of molten ISM.

According to one embodiment, the fixation vial (84) comprises at least one breakable seal towards the top of the vial, suitable for applying positive or negative air pressure therethrough. The fixation vial (84) may also comprise at least one breakable seal towards the top of the vial, suitable for receiving or removing fluid therethrough. The fixation vial (84) may also comprises at least one breakable seal towards the base of the vial, suitable for receiving fluid therethough.

In a preferred embodiment, the fixation solution vial is provided with a top lid (101) on which a sample holding means (102) and two breakable seals (92, 93) are provided for fluid and air access, and a breakable seal (105) on the base (106) of the vial for entry of the molten ISM. The seal on the base can be broken, for example, by a hollow tube inserted into the base. The hollow tube (95, FIG. 9) may protrude from the vial (86) carrying molten ISM, and allow molten ISM to flow therethrough. Preferably, the hollow tube (95) is located on the top of the ISM vial (86).

Vertically-Arranged Receiving Means

Figure 12:
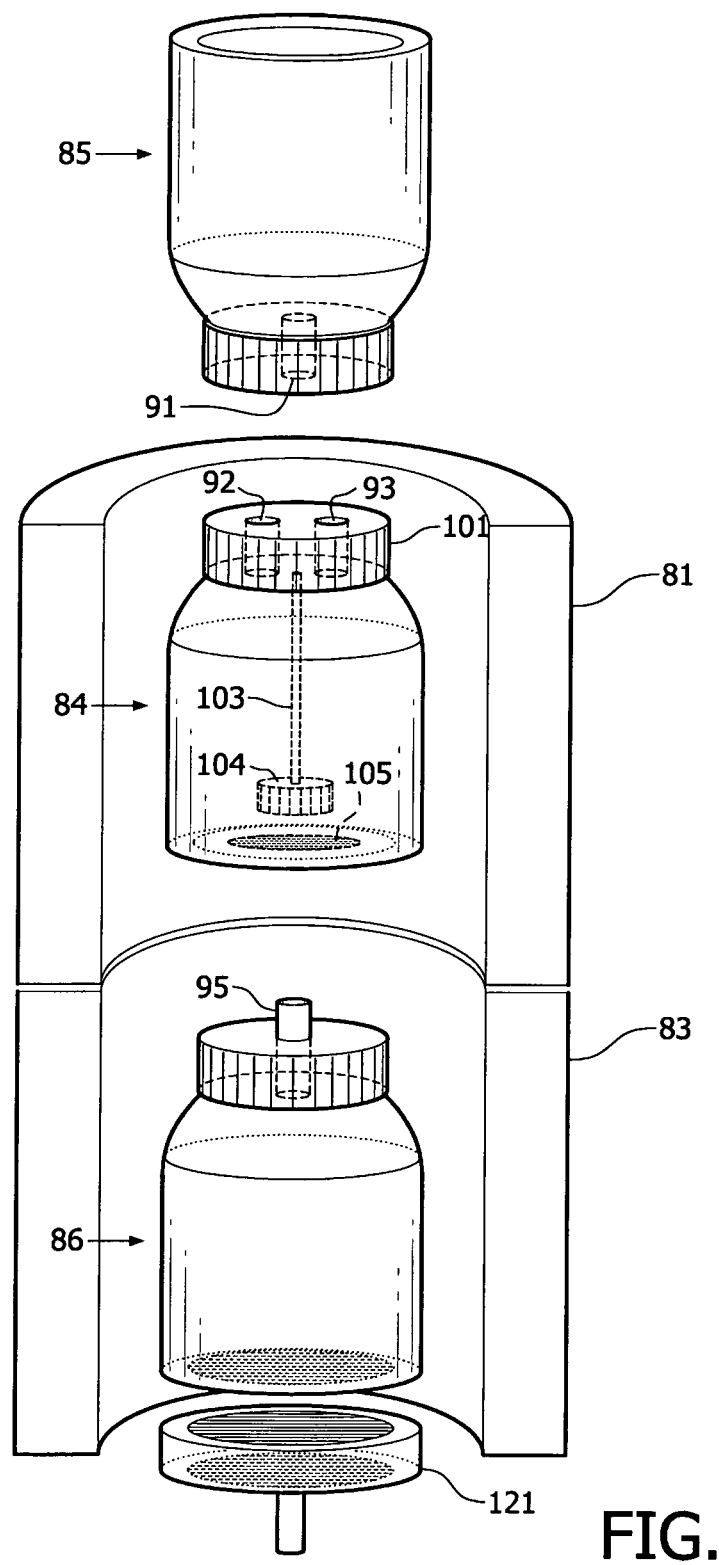
FIG. 12: Part of a preferred processing station where vials are vertically arranged.

According to one aspect of the invention, the respective vial receiving means are arranged essentially vertically along the same axis as shown, for example, in FIG. 12. Thus a column of essentially vertically arranged vial receiving means is formed. Preferably, the central axes of the vials are arranged essentially along a single axis. The fixation vial receiving means (81) can be placed in the centre of the column arrangement. Below may be placed the ISM vial receiving means (83) and above placed the clearing vial receiving means (not shown). The fixation vial receiving means (81) comprises fluid and air access means which can engage with the respective breakable seals (92, 93). The ISM vial receiving means (83) comprises a vertically moving platform (121) configured to move said vial (86) of ISM vertically. The platform which can move the vial (86) up and down to engage the hollow tube (95) on the top of the vial (described above) with a breakable seal (105) on the base of the fixation vial (84). Such platform can be operated hydraulically, by the use of levers, by rack-and-pinion assembly, or by any means known in the art. Both fixation vial receiving means (81) and ISM vial receiving means (83) comprise a cavity which walls are closely shaped to those of the vial and which contain means to heat or cool the sample. The clearing solution vial receiving means (not shown in FIG. 12) comprises a fluid access means which can engage with the vial.

The skilled person can readily implement a processing station as described above using, methods known in the art. The invention includes variations which the skilled person would implement in the course of carrying out the invention. The processing station can be configured with additional components to automatically perform the steps of fixation, clearing an impregnation. For example, a micro-processing means may co-ordinate the opening and closing of valves located between the access means. Such means and configurations are within the knowledge of the person skilled in the art implementing the invention.

Operation of the Processing Station

The following description refers to a mode of operation of a processing station. The skilled person can combine and adapt one of more the described steps according to the particular configuration chosen the processing station. During operation, the processing station is loaded with the vials containing fixation solution, clearing solution, and ISM. Upon loading, the seals in the vials can be broken by the respective vial receiving means where appropriate, and the fluid and optionally air access means of the processing station engage with the respective vials through the broken seals. The ISM vial receiving means is heated so as to melt the contents of the vial, while the fixation vial receiving means is preferably maintained at a lower temperature suitable for fixation and clearing. The sample is present in the fixation vial as described above. Once fixation has been completed as determined by time or by monitoring fixation using a crosslink indicator system, the fixation solution is removed by, for example, pumping air into the fixation vial and expelling the fixation solution out through the fluid access means into a waste jar. Clearing agent is then pumped into the fixation vial; this may be achieved by, for example, drawing air from the fixation vial via the air access means, and connecting the fluid access means of both the fixation and clearing receiving means. Thus clearing solution flows from the clearing solution vial to the fixation solution vial under vacuum. Once clearing is completed, the clearing solution is removed, for example, by pumping air into the fixation vial and expelling the fixation solution out through the fluid access means into a waste jar. The sample is then impregnated with molten ISM. This can be achieved as described above, for example, by drawing air from the fixation vial via the air access means, and connecting the fluid access means of both the impregnation and fixation vial receiving means. Where the processing station is arranged in a column fashion as described above, impregnation may proceed by raising the platform, and lifting the ISM vial. The tubular member pierces the breakable seal in the base of the fixation vial so forming a coupling. The movement may also open the breakable seal of the ISM vial. Once coupled, molten ISM can flow into the fixation vial by using, for example, vacuum pressure as described above. The temperature of the fixation receiving means can be raised during this step. After completion of impregnation, the molten ISM can be fed back into the ISM vial for cooling and disposal. Alternatively, it can be pumped into a waste jar.

A processing station according to the present invention is a simple and economic construction for processing a single sample, under precisely controlled conditions. Timings and volumes can be programmed, ensuring reproducibility across samples. The device uses vials containing predetermined concentrations and volumes of reagents which avoid the need for manual preparation and provides consistency between experiments and across different laboratories. In methods of the prior art, several samples are processed together in the same vessel, leading to mixing of cellular biomolecules such as, for example mRNA. The present device overcomes this problem by separately processing each sample. Because of the simplicity of construction, several processing station can be incorporated in a single device. The stations can share several components such as a processor, air and vacuum pump, waste lines etc, so even further reducing costs.

Data

Another aspect of the present invention is a tissue sample processed according to the method of the present invention. The sample can be distinguished from samples of the prior art because both cellular morphology and immunohistochemical profile are preserved, while degradation and modification of nucleic acids is limited.

Another aspect of the present invention is the data obtainable from a sample processed according to the method of the present invention. The data may be micrograph 2D or 3D (virtual) images of sections, morphological analysis data, nucleic acid concentration and integrity data and data from downstream nucleic acid analyses. The preserved sample may be prepared for nucleic acid analysis, or nucleic acid extracted from the sample using any suitable protocol known to those skilled in the art, e.g. Proteinase K digestion, followed by mild extract.

EXAMPLES

The following examples demonstrate the utility of the present invention. The described examples make use of fresh human surplus and experimental animal tissues or living cells in suspension. The methods and compositions of the current invention are applicable for tissue preservation for histopathological and molecular biological analysis for a broad range of animal (including human) and plant species. The examples are included to demonstrate preferred embodiments of the invention. However, the practice of the invention is not limited or restricted in any way by them.

Example 1

Exemplary General Manner of Tissue Processing

Tissue samples to be processed according to the current invention should be processed as quickly as possible after excision from the source after the onset of ischemia or death, or after removal from the soil or any other substrate solution or medium. In the case the samples posses a protective barrier that would interfere with FDC diffusion (e.g. a renal capsule or the waxy coating of plant material) this barrier should be removed prior to proceeding with the processing as described in the current invention. Large samples should be dissected/laminated into smaller fragments to maximize FDC diffusion in the first step of the present method. A general rule of thumb states the tissue thickness should not exceed 5 mm in at least one spatial dimension to allow proper fixation (Kiernan J P: Histopathological and Histochemical Methods, Theory, and Practice, ed 3. Oxford, Butterworth-Heinemann, 1999). Samples that consist of cell cultures should be carefully scraped from the culture flask and/or poured into a centrifuge tube. After centrifugation, a fibrin clot is generated that functions as a meshwork that keeps the cells in place. Once the specimen (artificial cell block, animal, human or plant tissue) is suitably fixed, dehydrated, cleared and infiltrated with ISM, it can be embedded in a casting ISM block according to the routine pathology laboratory procedures. The tissue samples treated according to the procedures described in the current invention, can be sectioned in an excellent manner, according to the routine procedures followed in a pathology laboratory (section thickness ranging from 3 μm to 30 μm). None of the following sectioning problems occur with specimens processed according to the method of the invention: embedding blocks are too soft or too hard and therefore difficult to section, indentation of the tissue in the ISM used to make the tissue block due to incomplete tissue dehydration, sections that tear, crumble or display striae, tissue ribbons that fail to form or are deformed. Section adhesion to glass slides is comparable to that of standard FFPE tissue sections and is accomplished by placing the slides overnight at 37 deg C. or for shorter periods at higher temperatures. The deparaffination procedures as employed for FFPE can be used on sections made from tissues processed according to the described invention. After deparaffination, the tissue sections can be rehydrated and used for histological or immunohistochemical staining, or processed directly for nucleic acid analysis. Advantage of the described method is that it will not cause a drastic reordering of the workflow in pathology laboratories (FIG. 1). Standardization of tissue fixation and processing using the described invention will ease comparison of specimens from different laboratories, this is of particular importance if samples collected at different local sites will be analyzed in a reference laboratory.

Example 2

The tissue morphological detail and cytology of tissues processed according to the current invention is as good as or better than FFPE tissues (e.g. prostate tissue and bronchoscopic biopsy).

A prerequisite for the general acceptance and introduction of the current invention into routine pathology, research and clinical laboratories is that tissues processed according to the described invention have a morphology comparable or superior to the one of FFPE tissues.

Figure 2:
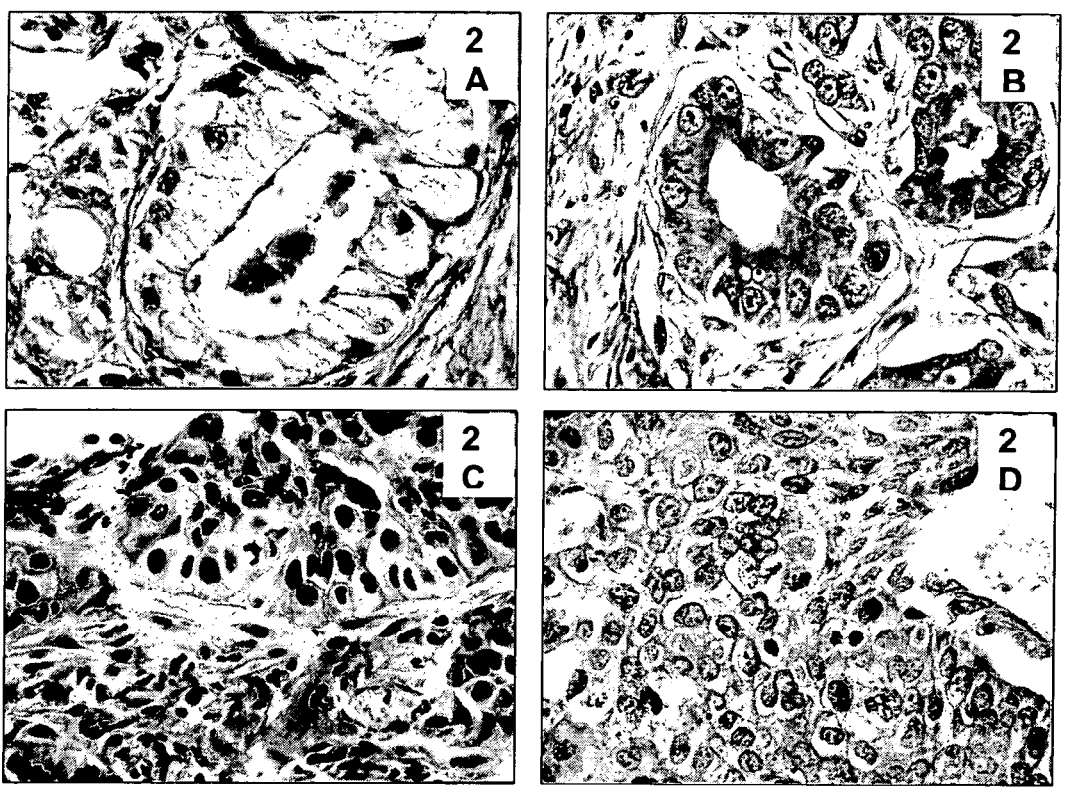
FIG. 2 shows the comparison between the tissue morphology of prostate tissue and a bronchus biopsy processed according to standard procedures (FFPE) and according to the described invention. The sections are stained with haematoxylin phloxine.

Typical examples that demonstrate the importance of preservation of good morphological detail for histopathological diagnosis are prostatic and bronchoscopic biopsies. Prostatic (FIGS. 2A and 2B) and bronchoscopic biopsies (FIGS. 2C and 2D) are shown. FIGS. 2A and 2C show biopsies processed according to standard routine pathology procedures (4% formalin fixation for 16 hours at room temperature, followed by tissue processing in a Leica Tissue Processor). FIGS. 2B and 2D show biopsies processed according to the procedures described in the current invention. There are no differences in sectionability between the routine FFPE blocks and paraffin blocks prepared according to the described invention. Both types of sections were automatically deparaffinized and stained with Hematoxylin Phloxin Saffranin according to routine procedures.

The prostatic biopsy (FIGS. 2A and 2B) contains tumoral glandular structures. The cytological detail of the tumor cell nuclei is characterized by the prominent nucleoli. The recognition of these cytological details is superior in the biopsy processed according to the procedures described in the current invention (FIG. 2B). The bronchoscopic biopsies (FIGS. 2C and 2D) contain a squamous cell carcinoma. The cytological detail of the tumor cell nuclei and mitotic figures is superior in the biopsy processed according to the procedures described in the current invention (FIG. 2D).

Example 3

Immunohistochemical (IHC) stainings performed on tissue processed according to the described invention and embedded in paraffin.

The antigenic profile of the samples processed according to the current invention should be comparable to the one of FFPE tissues. In addition, the antigen retrieval procedures that are applied to FFPE tissues should be applicable without any (or only minor) adaptations on material processed according to the described invention. Table 1 lists 85 antibodies (both monoclonal and polyclonal) that have been applied successfully on human surplus tissues processed according to the described invention. In total, 4239 sections were stained immunohistochemically and evaluated by pathologists, who found no differences between standard FFPE sections and sections from tissues processed according to the current invention. Data is shown in Table 1.

| Antibody target | Number of IHC stainings performed | Type of antibody |
| --- | --- | --- |
| ☐-1-antitrypsin | 10 | P |
| ☐-actin, sarcomeric | 6 | M |
| ☐-smooth muscle actin | 27 | M |

-continued

| Antibody target | Number of IHC stainings performed | Type of antibody |
|---|---|---|
| AFP | 10 | P |
| ALK | 13 | M |
| BCL-2 | 101 | M |
| Calcitonin | 1 | P |
| Calretinin | 36 | P |
| CD1a | 8 | M |
| CD10 | 83 | M |
| CD138 | 46 | M |
| CD15 | 64 | M |
| CD20 | 218 | M |
| CD23 | 19 | M |
| CD3 | 194 | M |
| CD30 | 131 | M |
| CD31 | 24 | M |
| CD34 | 16 | M |
| CD4 | 9 | M |
| CD45RB | 173 | M |
| CD5 | 73 | M |
| CD68 | 64 | M |
| CD79a | 21 | M |
| CD8 | 7 | M |
| CD99 | 3 | M |
| CEA | 159 | M |
| Chromogranin | 2 | M |
| Chromogranin A | 53 | M |
| CK1, 5, 10, 14 | 171 | M |
| CK14 | 83 | M |
| CK2, 5, 6, 8, 15, 18, 19 | 98 | M |
| CK20 | 135 | M |
| CK5, 6 | 37 | M |
| CK7 | 248 | M |
| CK8 | 106 | M |
| CMV | 12 | M |
| Cyclin D1 | 26 | M |
| Desmin | 16 | P |
| E-cadherin | 14 | M |
| EBV-LMP1/CS 1-4 | 15 | M |
| EMA | 213 | M |
| ER | 216 | M |
| GFAP | 29 | P |
| Glycophrin C | 2 | M |
| HAM56 | 1 | M |
| Helicobacter | 19 | P |
| HepBcAg | 32 | P |
| HepBsAg | 37 | P |
| HMB45 | 15 | M |
| HPV | 1 | P |
| HSV1 | 8 | P |
| HSV2 | 6 | P |
| KAPPA | 19 | P |
| Ki-67 | 2 | M |
| Lambda | 19 | M |
| Lysozyme | 2 | P |
| Mycobacteria | 67 | P |
| Myeloperoxidase | 8 | P |
| Myoglobin | 1 | M |
| Neu | 336 | P |
| Neurofilament | 13 | M |
| NSE | 30 | M |
| p53 | 9 | M |
| PCNA | 2 | M |
| Pneumocystis carinii | 16 | M |
| PR | 218 | M |
| PSA | 37 | P |
| PSAP | 33 | P |
| S100 | 80 | P |
| Synaptophysin | 2 | M |
| Synaptophysin | 36 | P |
| Tdt | 3 | M |
| Thyroglobulin | 6 | P |
| TTF-1 | 112 | M |
| Ubiquitin | 19 | P |
| Vimentin | 37 | M |
| CD117 | 8 | P |
| CD57 | 2 | M |
| CD18 | 1 | M |
| Collagen type IV | 1 | P |
| Fibrinogen | 2 | P |
| HCG | 1 | P |
| Myf-4 | 1 | M |
| Myoglobin | 2 | P |
| PLAP | 3 | M |

P = polyclonal
M = monoclonal

Example 4

FDA-approved HER-2 immunostaining of human surplus segments of breast tumor biopsies, processed according to the current invention.

A surplus breast cancer sample was prepared using a method of the present invention. It was incubated in FDC solution comprising 10% (v/v) formaldehyde, 65% (v/v) methanol, 5% (v/v) acetic acid and 20% (v/v) diethylether. The surplus sample was subsequently treated with clearing solution comprising diethylether, and then embedded in molten paraffin at 52 deg C.

Figure 3:
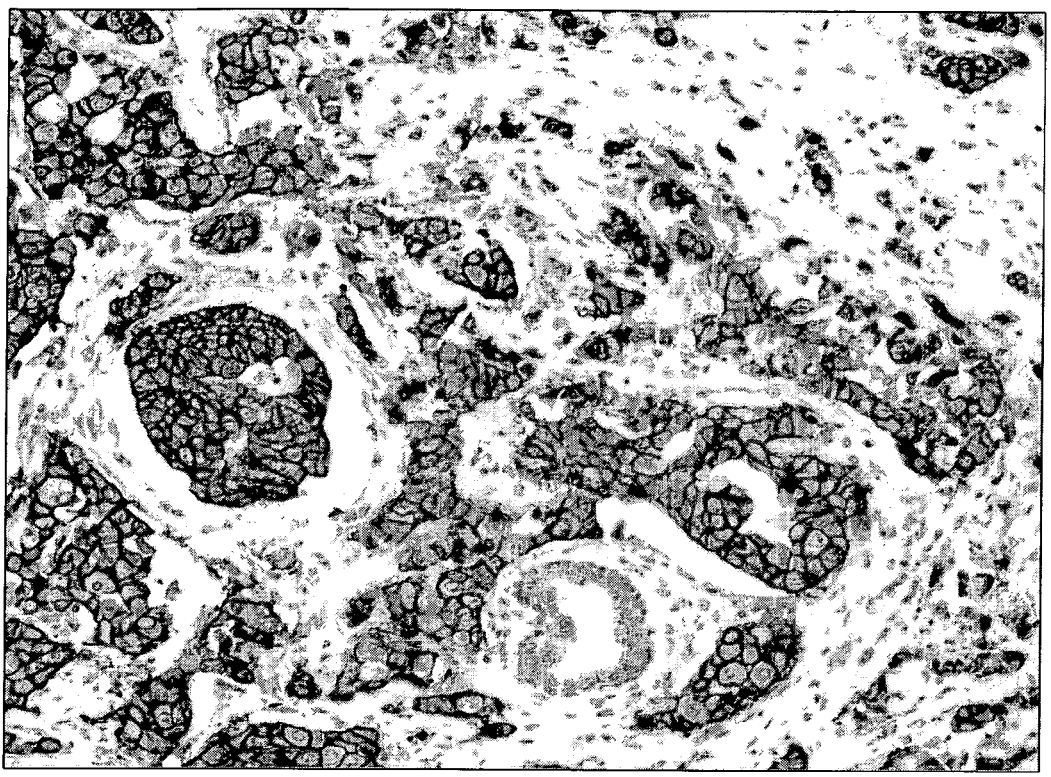
FIG. 3 shows a FDA-approved HER-2 immunostaining performed on a breast tumor biopsy, processed according to the procedure as described in the invention.

There were no differences in sectionability between the routine FFPE blocks and paraffin blocks prepared according to the described invention. Pathologists found the morphological quality of the tissue samples processed according to the described invention to be good to very good. IHC stainings for hormone receptors and the growth factor receptor HER-2 could be performed with the protocol described for standard FFPE tissues. FIG. 3 shows a strong membrane staining for HER-2 (chicken wire pattern) which indicates score 3+. This result was similar with the result obtained on the FFPE sample of the same tumor. This is important as the HER-2 immunodetection is an "FDA-approved test". This means that every important alteration/adaptation of the staining procedure would invalidate the test.

Example 5

IHC staining of antigens that are very sensitive for fixation artefacts e.g. phosphoproteins and/or phosphorylation-sites can also be performed on sections prepared according to the methods of the invention.

Figure 4:
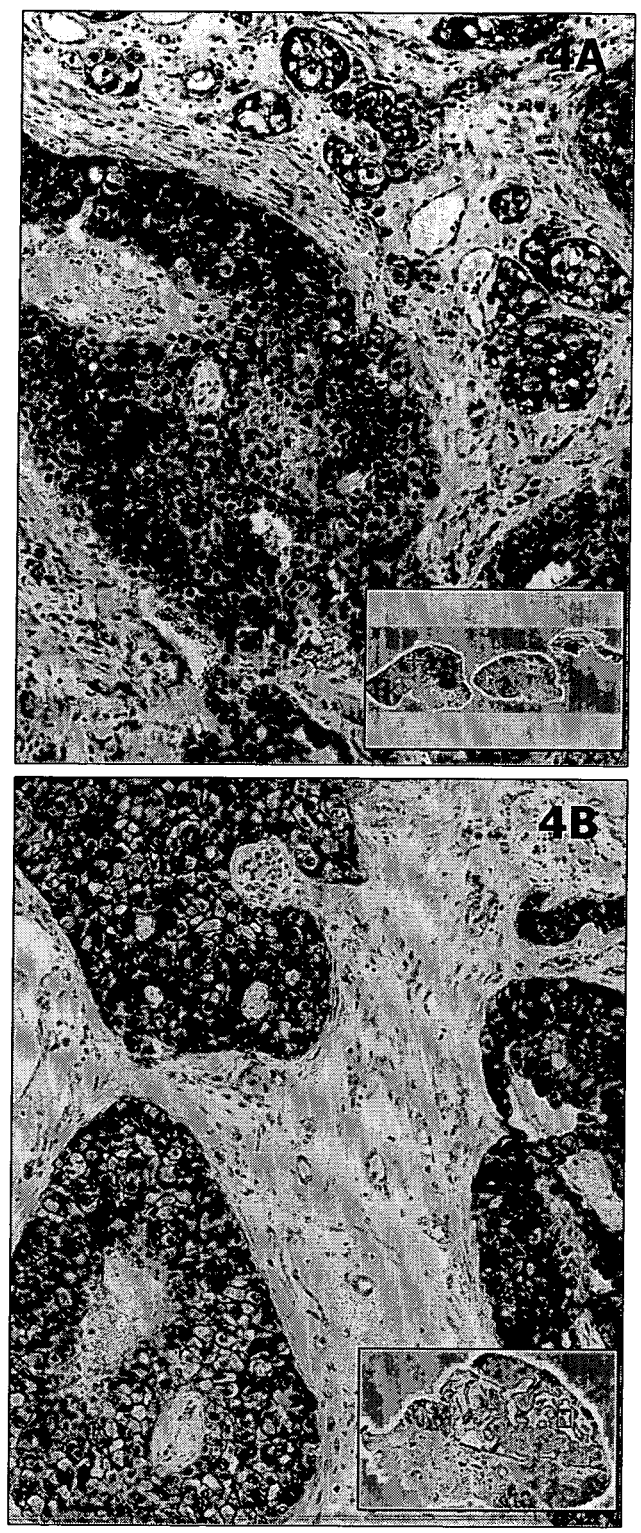
FIG. 4 shows immunohistochemical staining of phosphorylated AKT (pAKT), performed on breast tumor specimens: comparison of FFPE tissue and specimens processed according to the current invention.

Commercial phosphorylation state-specific antibodies are available for more than 300 different phosphoproteins and/or phosphorylation-sites (Mandell J W: Phosphorylation state-specific antibodies. Applications in investigative and diagnostic pathology. Am J Pathol 163: 1687-1698, 2003). Important here is the transient nature of the phosphorylation state, since protein phosphorylation is a very dynamic process. It has been shown that post-mortem conditions and tissue resection, can influence the phosphorylation state (Song J, Combs C K, Pilcher W H, Song L Y, Utal A K, Coleman P D: Low initial tau phosphorylation in human brain biopsy samples. Neurobiol Aging 18: 475-481, 1997). In addition, it seems that for some phosphoproteins e.g. pERK, the diffusion of formalin is too slow to maintain the phosphorylation state in the core of the biopsy. The composition of FDC is such that it allows the investigation of the phosphorylation state. As is demonstrated in FIG. 4, pAKT immunostaining of FFPE breast tumors and bronchus biopsies results in diffuse cytoplasmic signals (FIG. 4A), while pAKT staining of breast tumors and bronchus biopsies processed according to the current invention results in crisp membrane signals (FIG. 4B).

Example 6

Fluorescent in situ hybridisation (FISH) can be performed on sections prepared according to the methods of the invention.

Figure 5:
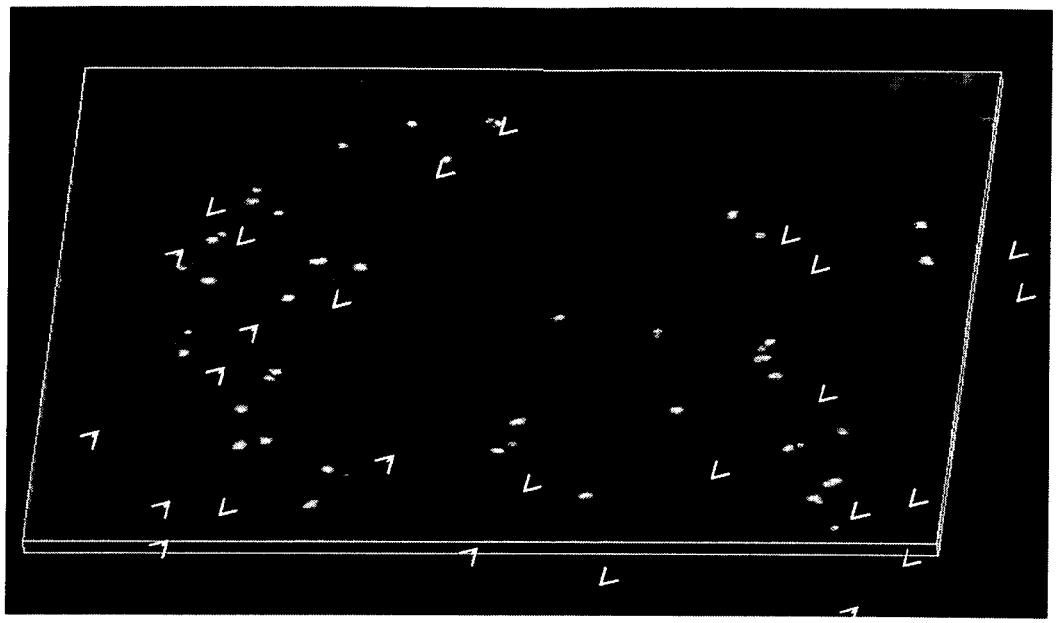
FIG. 5 shows fluorescent in situ hybridisation (FISH) for the HER-2 gene performed on a breast tumor specimen processed according to the current invention.

Target retrieval techniques such as heating and proteinase K digests are current tissue pre-treatment practice for FISH detection of genes on FFPE samples. In our hands, the variations that occur during the pre-analytical phase (use of different formulations of formalin, different fixation times, different dehydration and embedding procedures, . . . ) necessitate sample-to-sample optimisation of the section pre-treatment. FISH for the HER-2 gene (FDA-approved test) can be performed on sections prepared according to the methods of the invention. Data is shown in FIG. 5 which depicts a section of breast tumor sample processed according to the method of the present invention in which HER-2 gene is indicated. Data shows a higher signal/background ratio and a broader fixation window.

Example 7

Chromogenic in situ hybridisation (ISH) can be performed on tissues processed according to the described invention without adaptations of the hybridisation protocol used for FFPE tissues.

Figure 6:
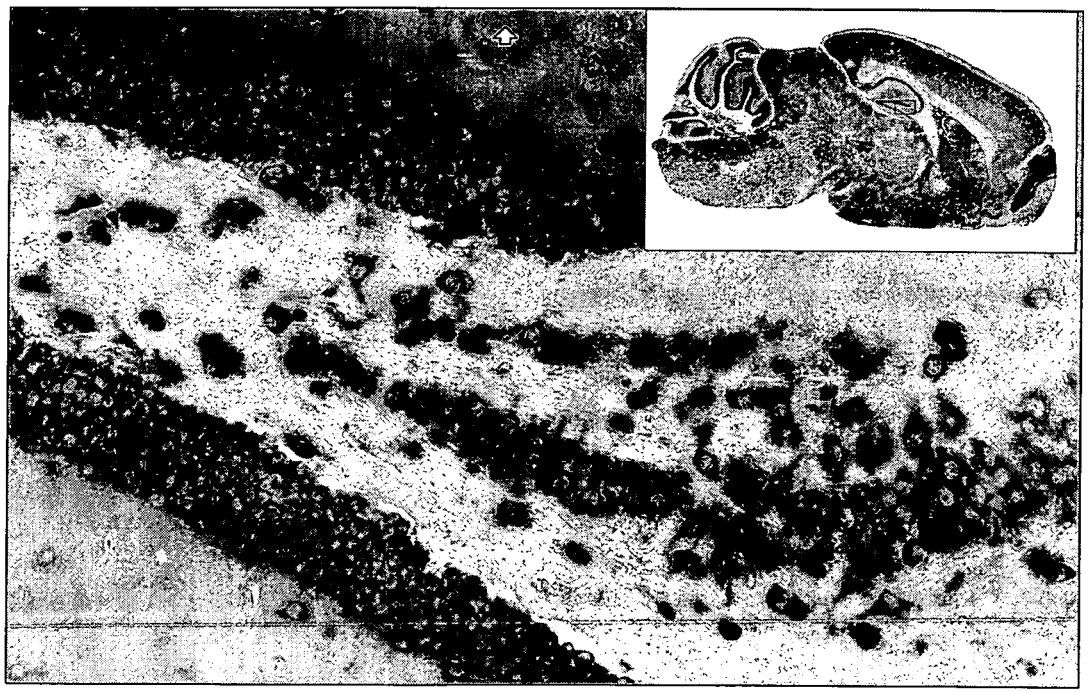
FIG. 6 shows a chromogenic in situ hybridisation (ISH) for 28S rRNA on a mouse brain processed according to the current invention. Hybridisation signals were demonstrated with standard alkaline phosphatase nitroblue tetrazolium salt/5-bromo-4-chloro-indolyl phosphate (NBT/BCIP) detection.

ISH was performed for 28S rRNA on a mouse brain processed according to the method of the current invention. Hybridisation signals were demonstrated with standard alkaline phosphatase NBT/BCIP detection. Data is shown in FIG. 6. In the hippocampal region of the mouse brain, the cytoplasm of nerons in hippocampus and gyrus dentatus shows strong hybridisation signals.

Example 8

Chromogenic ISH can be performed on artificial tissue cell blocks prepared from transfected cell lines according to the current invention.

Figure 7:
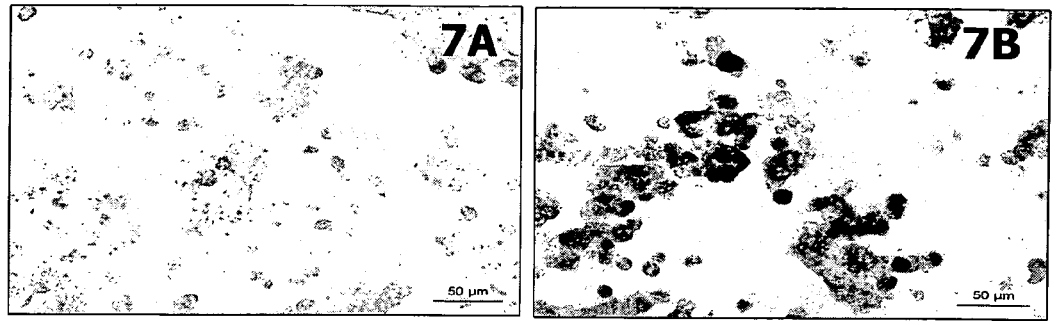
FIG. 7 shows that a chromogenic ISH can be performed on an artificial tissue cell block prepared from a transfected cell line according to the described invention. ISH was performed for the transcript encoding for the transfected protein. Hybridisation signals were demonstrated with standard alkaline phosphatase NBT/BCIP detection.

ISH was performed for the transcript encoding the transfected protein. Hybridisation signals were demonstrated with standard alkaline phosphatase NBT/BCIP detection. Sections prepared according to the described invention are shown in FIG. 7. Sections (FIG. 7A) are completely negative after hybridisation with the sense (negative control) probe and clear-cut hybridisation signals (FIG. 7B) are obtained with the antisense probe.

Example 9

Total RNA can be extracted from paraffin sections prepared according to the method of the described invention.

Two sections (10 µm thickness) of a rat liver tissue block processed according to the current invention were made nuclease-free, using disposable blades. The tissue block was prepared according to the present invention as described in Example 1. All following procedures were performed under nuclease-free conditions. The sections were collected in nuclease-free tubes, deparaffinized, and the remaining tissue was washed in isopropanol. The tissue was subsequently digested for 3 hours with proteinase K and the digested tissue components were ethanol-precipitated. The precipitated cell components were then resuspended and homogenized in a highly denaturing guanidine isothiocyanate-containing buffer, which immediately inactivates ribonucleases to ensure the isolation of intact RNA. Synthetic nucleic acid, in the form of polyinosinic acid, is added as carrier material to reduce loss of RNA during the extraction procedure. Ethanol is then added to provide appropriate binding conditions, and the sample is then applied to a silica-based membrane in spin column format. The total RNA binds to the column and contaminants are washed away. The RNA is then eluted in nuclease-free water. A kit that can be used for the RNA extraction is e.g. the RNeasy Mini or Micro kit from Qiagen (Hilden, Germany).

Figure 13:
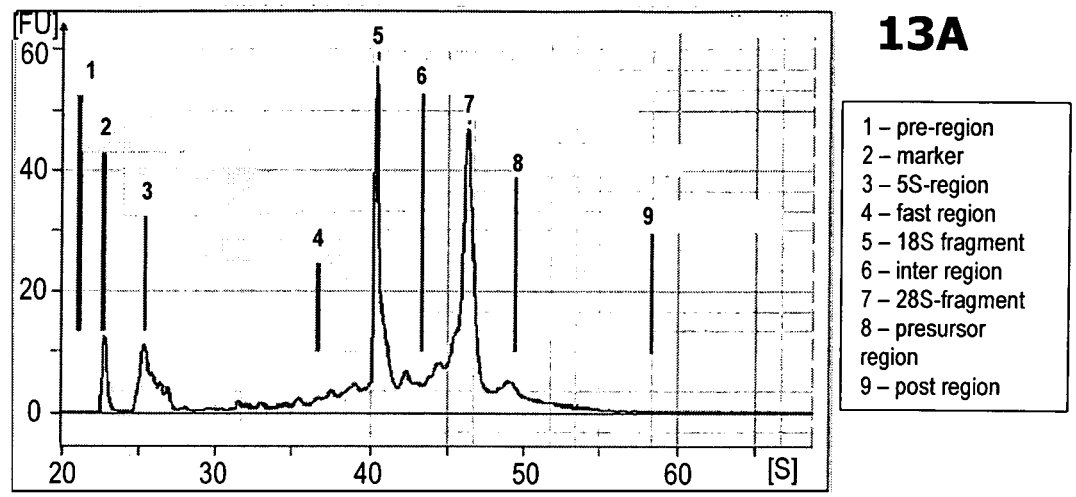
FIG. 13 shows an explanatory scheme of a total RNA BioAnalyzer profile, an example of a total RNA profile from intact RNA isolated from experimental rat liver cryosections and an example of a total RNA profile from RNA isolated from rat liver paraffin sections prepared according to the current invention.
Figure 13:
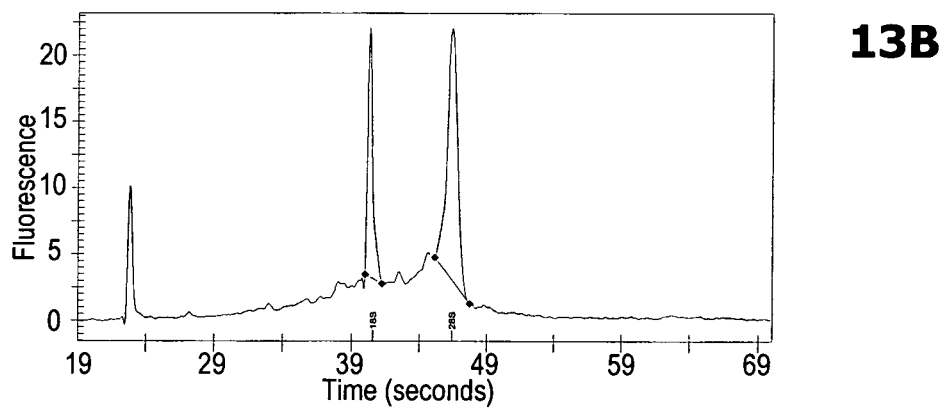
Figure 13:
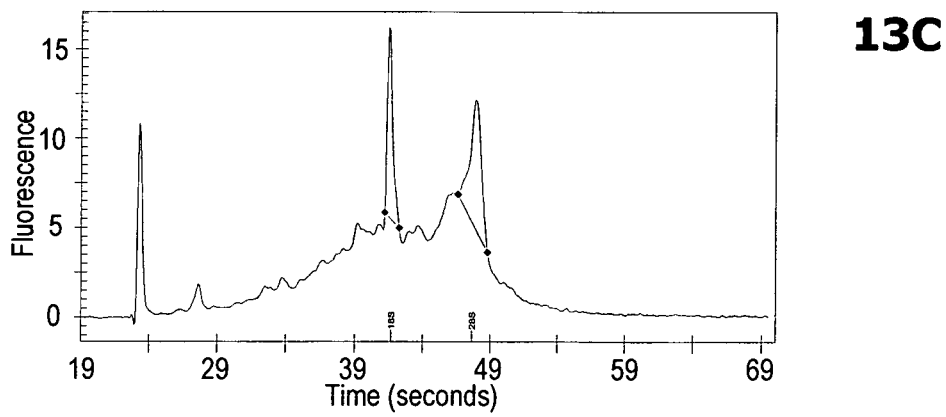

The assessment of RNA integrity is a critical first step in obtaining meaningful gene expression data. Using intact RNA is a key element for successful microarray or RT-PCR analyses. The Agilent 2100 bioanalyzer and RNA LabChip® kits were used for the determination of RNA quality. Profiles generated on the Agilent 2100 bioanalyzer yield information on concentration, allow a visual inspection of RNA integrity, and generate ribosomal ratios. The bioanalyzer software generates both an electropherogram and gel-like image. The electropherogram provides a detailed visual assessment of the quality of an RNA sample. An example of such a total RNA profile with its different subregions is shown in FIG. 13A. Previously, researchers have used the ribosomal ratio in both slab gel analysis and as a feature within the bioanalyzer software to characterize the state of RNA intactness. Slab gel analysis of total RNA samples using ribosomal ratios often results in an inaccurate assessment of the RNA integrity. The Agilent 2100 bioanalyzer provides a better assessment of RNA intactness by showing a detailed picture of the size distribution of RNA fragments (FIG. 13A). RNA degradation is a gradual process. As degradation proceeds, there is a decrease in the 18S to 28S ribosomal band ratio and an increase in the baseline signal between the two ribosomal peaks and the lower marker. The RNA Integrity Number (RIN), was developed to remove individual interpretation in RNA quality control. Using this tool, sample integrity is no longer determined by the ratio of the ribosomal bands alone, but by the entire electrophoretic trace of the RNA sample (FIG. 13A), including the presence or absence of degradation products. In this way, interpretation of an electropherogram is facilitated, comparison of samples is enabled and repeatability of experiments is ensured.

A BioAnalyzer RNA profile from intact total RNA isolated from experimental rat liver cryosections is shown in FIG. 13B as a reference. This sample had a RIN of 8.2 and a yield of 1.7 ng/mm$^2$ tissue. A BioAnalyzer RNA profile from total RNA isolated from experimental rat liver paraffin sections prepared according to the current invention is shown in FIG. 13C. The sample prepared according to the current invention had a RIN of 7.1 and a yield of 3.6 ng/mm$^2$ tissue.

Example 10

Comparison of the quality of total RNA isolated from cryosections versus paraffin section prepared according to the current invention versus FFPE human "mirror" sections.

Figure 14:
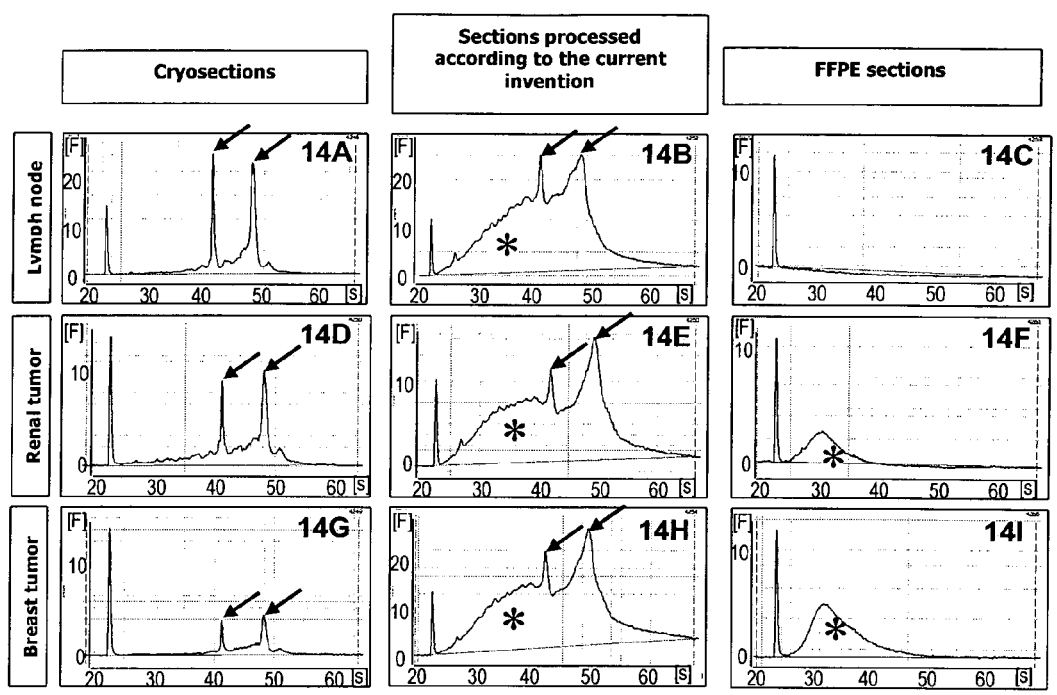
FIG. 14 shows the comparison of the quality of total RNA isolated from cryosections and from FFPE and human "mirror" samples processed according to the current invention.

Human lymph node (FIGS. 14A, 14B, 14C), renal tumor (FIGS. 14D, 14E, 14F) and breast tumor (FIGS. 14G, 14H, 14I) tissue were processed in the pathology laboratory. After lamination, a representative segment was cryoprocessed (snap-frozen and embedded in O.C.T. compound) for rapid diagnosis, several representative segments were formalin-fixed and paraffin-embedded according to routine pathology protocols for more detailed diagnosis and a surplus segment was processed according to the procedure as described in the invention. Therefore, we could compare the RNA quality of triplet segments derived from a single specimen (identical agonal state, therapy and post-ischemic interval). Sections were made nuclease-free and all following procedures were performed under nuclease-free conditions. Total RNA was extracted and analyzed according to the procedure described in example 9. The duration of the proteinase K digestion was optimized for both paraffin sections from the current invention and FFPE sections. For RNA extraction from cryosections, the procedure performed was basically the same as for paraffin sections with the omission of the deparaffination and proteinase K digestion steps. The total RNA profiles are depicted in FIG. 14. As can be seen from FIGS. 14A, 14D and 14G, the total RNA isolated from frozen sections was of excellent quality for the 3 tissue types tested (RIN values respectively 9.3; 7.5 and 8.3). These RNA samples represent the "initial RNA quality" of the human tissues, which is of critical importance because the golden rule "garbage in, garbage out" also applies to tissue fixation. The RNA isolated from paraffin sections prepared according to the current invention (FIGS. 14B, 14E and 14H) is of good quality, i.e. the RNA profiles display clear rRNA peaks (arrows), but the RIN values could not be determined due to shifted baselines (N/A). There is some RNA degradation as can be seen from an increase of the RNA species with shorter fragment length (stars). The RNA isolated from FFPE sections (FIGS. 14C, 14F and 14I) is of very poor quality, i.e. the RNA profiles display no rRNA peaks at all, only short fragment RNA species are detected (stars) and the RIN values are low (respectively N/A, 2.2 and 2.2).

Example 11

RT-qPCR on breast tumor tissue processed according to standard procedures (FFPE) or according to the current invention.

A breast cancer biopsy was FFPE and a similar surplus sample was prepared using a method of the present invention. The latter was incubated in FDC solution comprising 10% (v/v) formaldehyde, 65% (v/v) methanol, 5% (v/v) acetic acid and 20% (v/v) diethylether. The surplus sample was subsequently treated with clearing solution comprising diethylether, infiltrated in low-melting paraffin at 52 deg C. and embedded in casting paraffin.

Figures 1, 15:
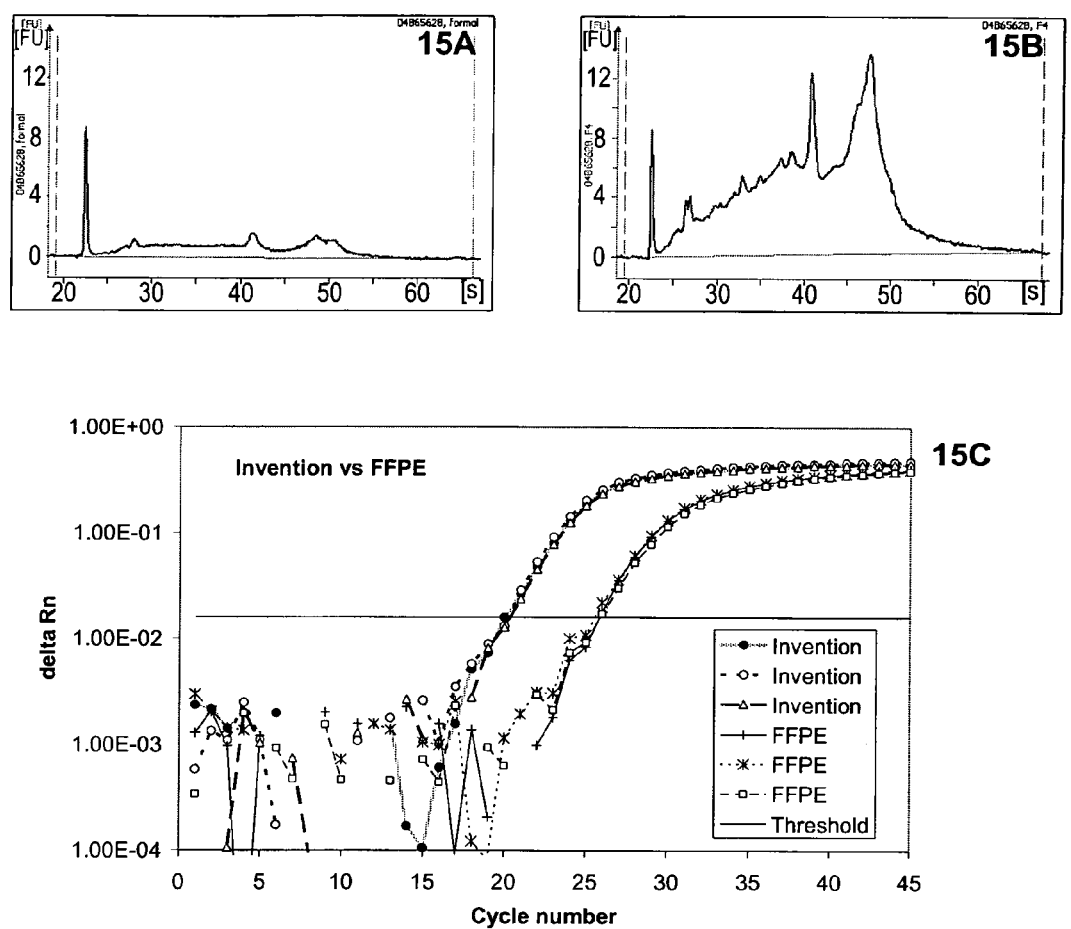
FIG. 15 shows the results from RT-qPCR for Her-2/Neu performed on FFPE breast tumor versus "mirror" surplus samples processed according to the described invention. A comparison between a Her-2 negative and Her-2 positive breast tumor processed according to the current invention is also shown.
Figures 2, 15:
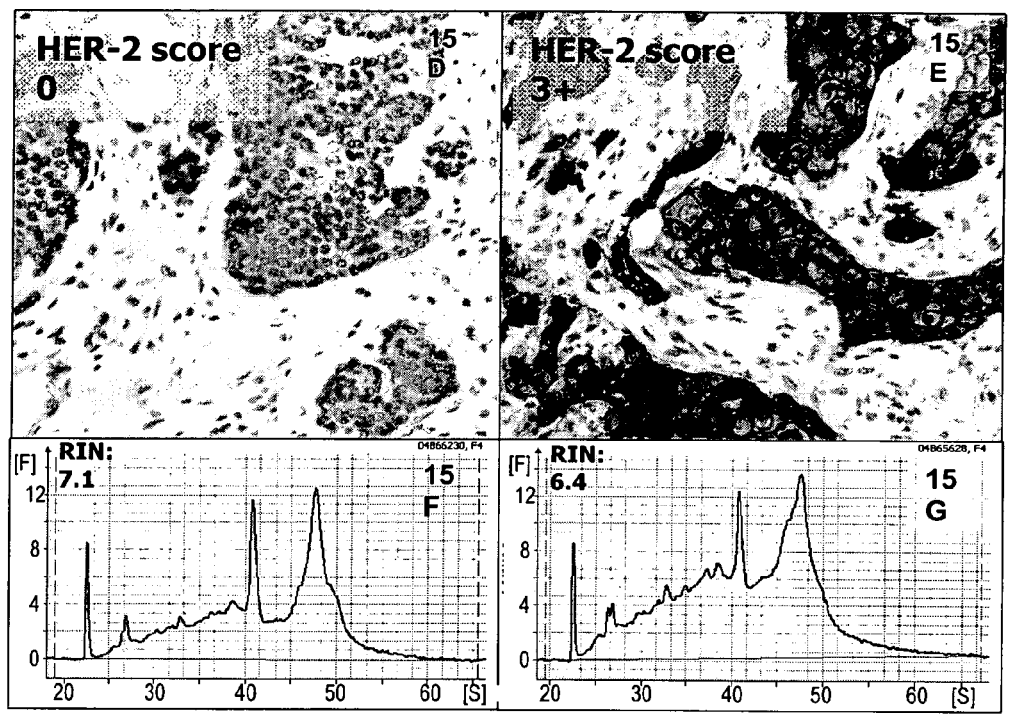
Figures 3, 15:
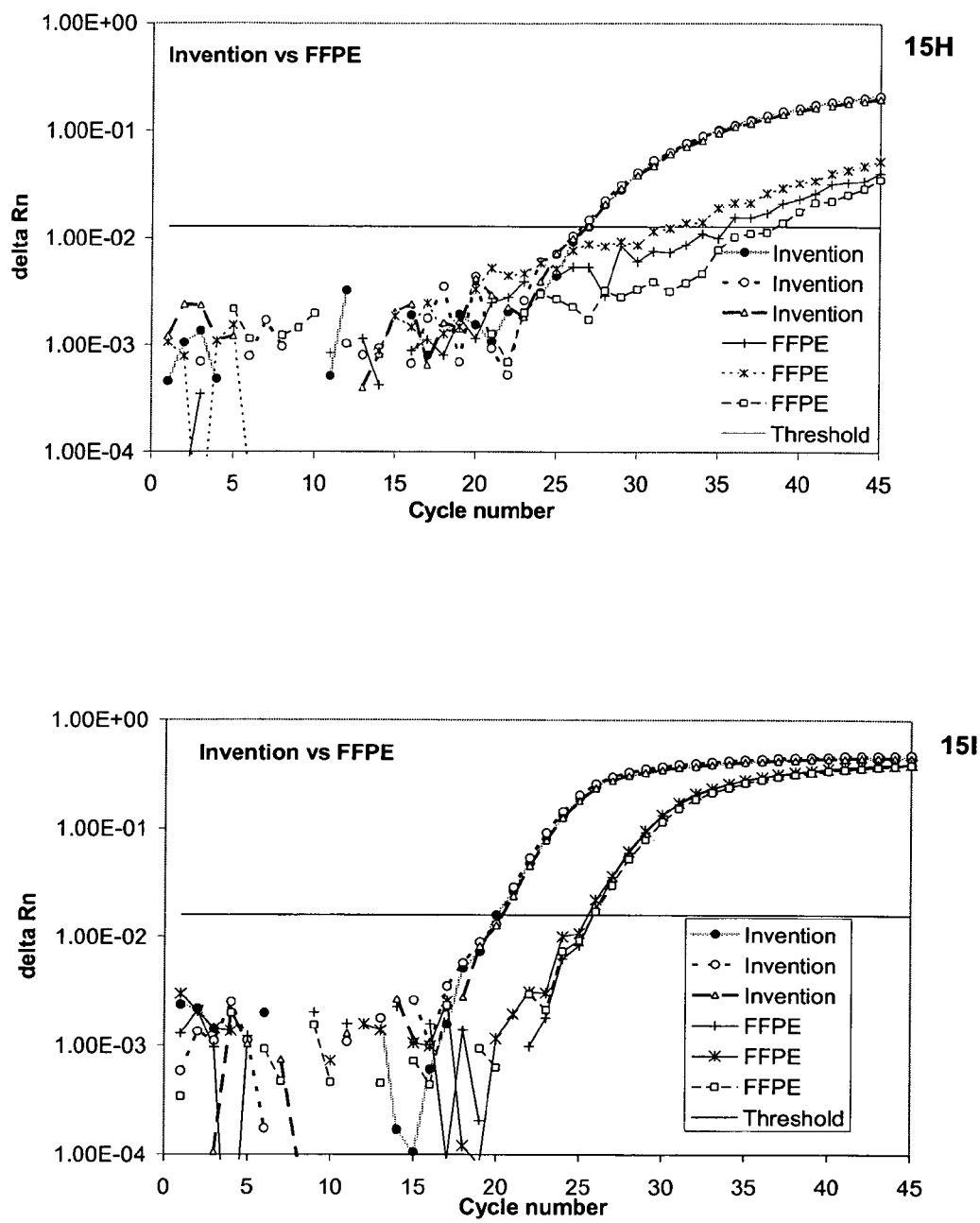

Sections were made nuclease-free and all following procedures were performed under nuclease-free conditions. Total RNA was extracted according to the procedure described in Example 10. RNA quality was evaluated as demonstrated in Examples 9 and 10. The RNA integrity number and RNA concentration were determined for both treated samples using the Agilent RNA profiling technology as described in Example 9. FIG. 15A shows the RNA profile obtained from FFPE sections, FIG. 15A shows the RNA profile obtained from a sample treated using methods of the current invention. Using the classical FFPE method, the RIN was 4.2 and the RNA concentration per $mm^2$ tissue was 70 ng/µl. Using the present invention, the RIN was 6.4 and the RNA concentration per $mm^2$ tissue was 360 ng/µl. So both RNA yield and quality were poorer in FFPE tissue than in tissue processed according to the current invention.

In a further test, the RNA extract from both samples was tested for the expression of the Her-2/neu gene using reverse transcription and quantitative real-time PCR (RT-qPCR). The results shown in FIG. 15C, roughly indicate a $2^{(25.7-20.2)}$ or 45 times higher concentration of the Her-2/neu transcript in the sample treated according to the present invention compared with FFPE.

In addition, a comparison was made between a two breast cancer biopsies processed according to the current invention—one that is HER-2 negative (FIG. 15D) and another that is HER-2 positive (score 3+, FIG. 15E). RNA was extracted and analyzed according to Examples 9 and 10. As can be seen in FIGS. 15F and 15G, both samples have total RNA of good quality (intact ribosomal peak profile) with respective RIN values of 7.1 and 6.4. Both samples were tested for the expression of the Her-2/neu gene using reverse transcription and quantitative real-time PCR (RT-qPCR). The results shown in FIGS. 15H and 15I, roughly indicate a $2^{(27-20)}$ or 128 times higher concentration of the Her-2/neu transcript in the HER-2 positive sample than in the HER-2 negative sample.

Example 12

Fragment length of PCR products amplified from DNA isolated from cryosections compared to paraffin sections prepared according to the methods of the invention.

Figure 16:
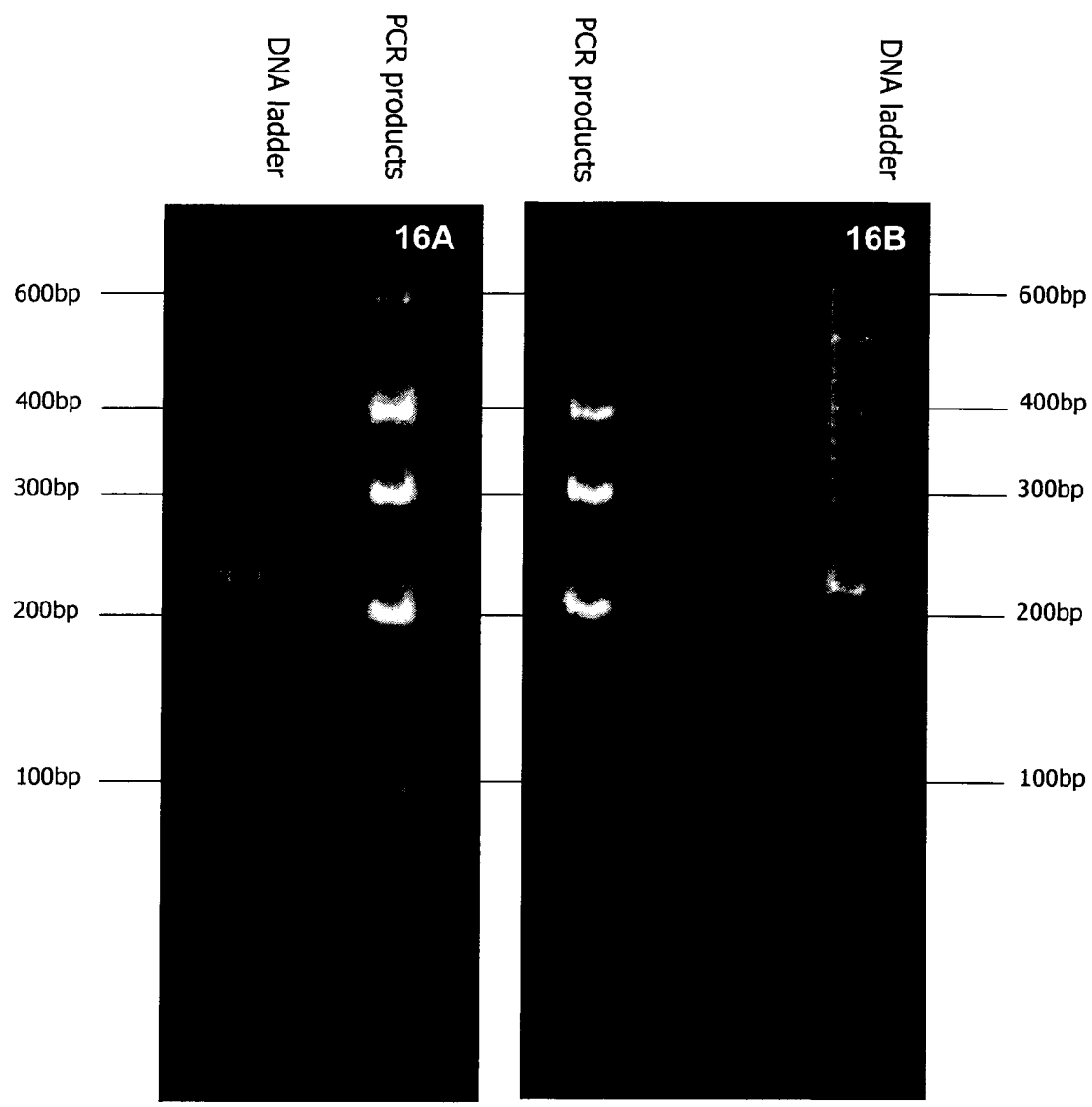
FIG. 16 shows a polyacrylamide gel loaded with amplicons generated with DNA isolated from falsh-frozen versus "mirror" surplus tissue samples processed according to the described invention.

DNA was isolated from the nuclease-free cut sections (e.g. with the Dneasy kit from Qiagen, Hilden, Germany). Control multiplex PCR was performed for the evaluation of the quality and amplifiability of DNA extracted from lymphomas. The PCR products were separated electrophoretically. FIG. 16A shows PCR products generated with DNA extracted from a cryosection. Amplicons with a fragment length of 600 bp are clearly visible. FIG. 16B shows PCR products generated with DNA extracted from a paraffin section prepared according to the current invention. Amplicons with a fragment length of 400 bp are clearly visible, small amounts of PCR products with a length of 600 bp are still present.

Example 13

Her/Neu DNA amplification on breast tumor tissue processed according to standard procedures (FFPE) or according to the current invention.

Figure 17:
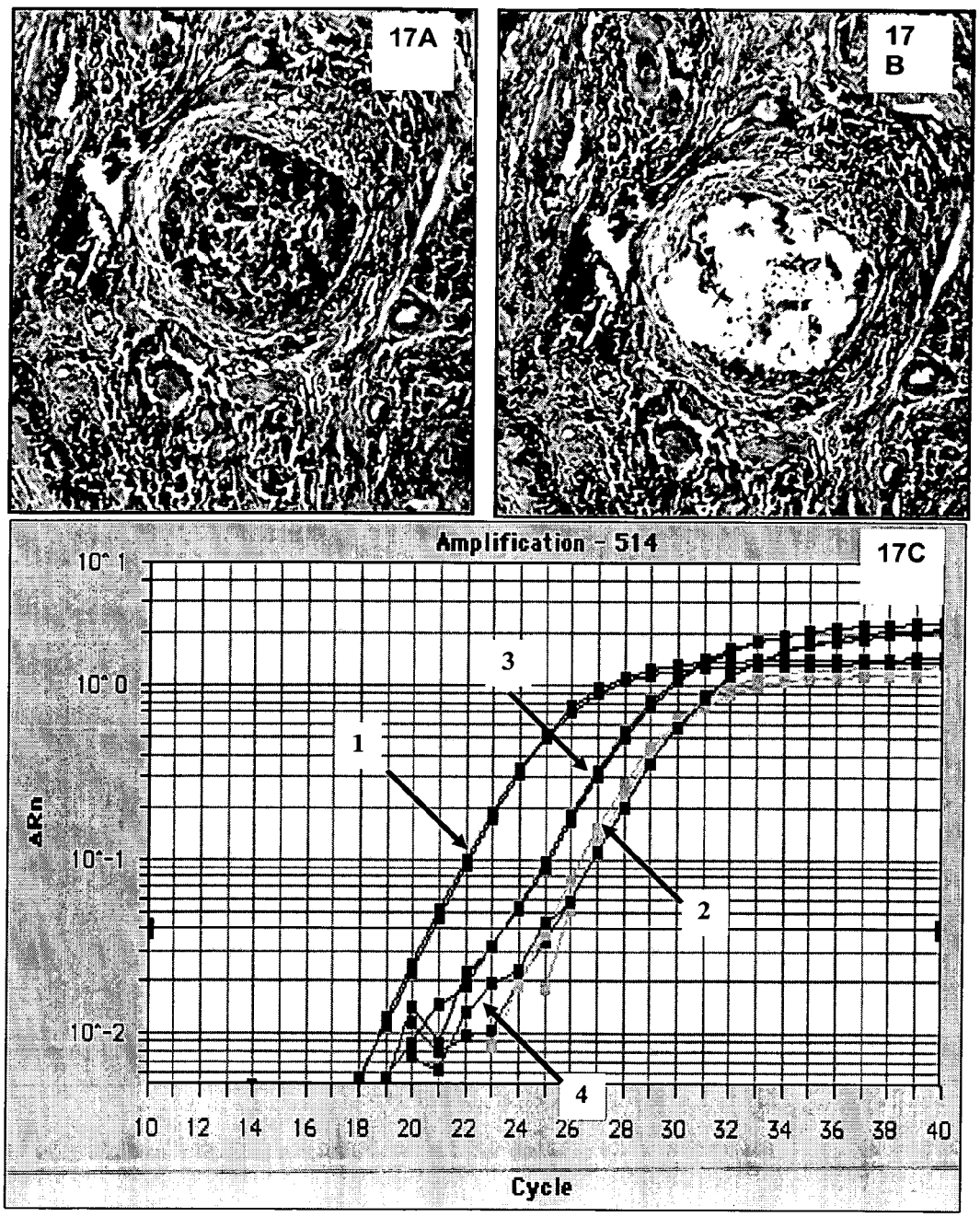
FIG. 17 shows the results from qPCR for the Her/Neu gene performed after laser capture microdissection of tumor cells from breast tumor tissue processed according to the described invention.

Breast tumor sections prepared according to the current invention and sectioned under nuclease-free conditions were stained with a nuclear histological stain (MethylGreen) and tumor cells were laser capture microdissected (LCM). All procedures were performed under nuclease-free conditions. FIG. 17A shows the section before LCM and FIG. 17B shows the section after LCM isolation of a tumor nest. DNA was isolated from the captured cells (e.g. with the Dneasy kit from Qiagen, Hilden, Germany) and Her-2/Neu DNA amplification was analysed with qPCR (FIG. 7C). Plots 1 and 2 (light plot) are the amplification plots for Her-2 gene and plots 3 and 4 (dark plot) are the amplification plots for the reference gene. Amplification plots 1 and 3 correspond with the IHC Her-2 positive tumor and amplification plots 2 and 4 correspond with the HER-2 negative tumor. While the plots for the reference gene are practically identical for both breast tumor samples, the amplication plot of the Her-2+ tumor has clearly shifted to the left, which clearly indicates that a larger number of copies of the Her-2 gene are present in the Her-2+ tumor prepared according to the current invention.

Example 14

RNA quality from sections stained histologically (nuclear stainings) for laser microdissection (LCM): comparison of the quality of RNA derived from cryosections versus paraffin sections prepared according to the current invention before LCM.

The recognition of cellular heterogeneity is fundamental for any effective gene expression strategy for solid tissue specimens. Failure to take this diversity into account invariably leads to averaging of the genetic information contained within different cell types within a tissue. A technique that represents the ultimate harmonization between the two disciplines of histopathology and molecular biology is laser microdissection (LCM). LCM allows for the selective collection of cells of interest from heterogeneous tissue sections. To identify the specific cells for LCM, conventional histological stains, as well as immunohistochemical or immunofluorescent labelling have been used. LCM is performed on histological sections that are not cover-slipped. This results in reduced cellular detail, which diminishes the ability to distinguish different cell populations. Ideally, histochemical stains should provide acceptable morphology in order to enable LCM of the correct cell type. In addition, the stain should not interfere with the macromolecules of interest or the subsequent techniques used for molecular analysis. Some cell types (e.g. tumor cells) can be distinguished from surrounding heterogenous cell populations after a simple histological nuclear staining on the basis of their nuclear morphology. If nuclear acid analyses are to be performed after laser capture microdissectie (LCM) of the relevant cell population, it is of critical importance that the stainings are performed quickly and nuclease-free, to prevent RNA depletion and degradation.

Figure 18:
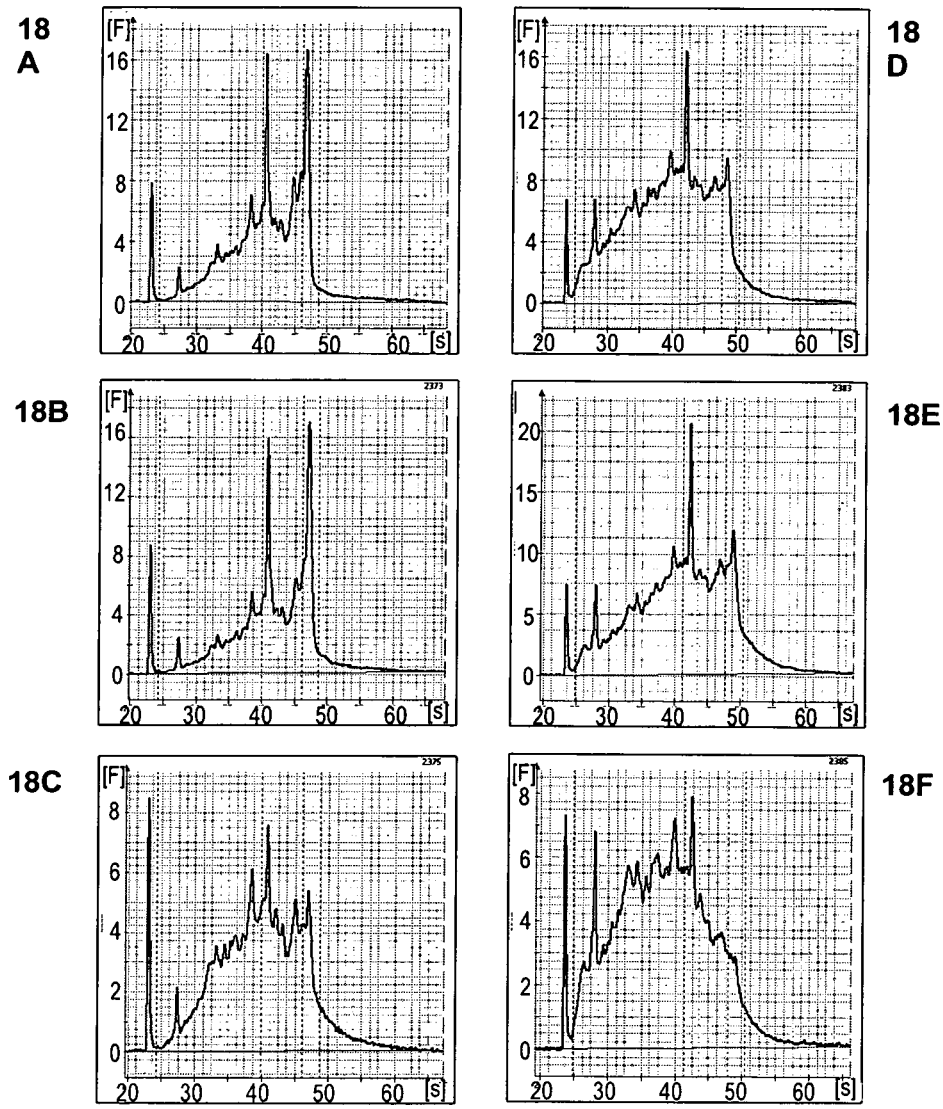
FIG. 18 shows the comparison of the quality of total RNA isolated from histological stained rat liver sections for LCM (different nuclear stainings). The RNA extracted from complete cryosections and from paraffin sections prepared according to the current invention were compared.

Short nuclease-free nuclear stainings were optimized for LCM with the Arcturus PixCell II system. Twin samples of rat liver were flash-frozen end embedded in O.C.T.-compound or processed according to the current invention. All sections were made nuclease-free and all procedures were performed under nuclease-free conditions. Cryosections were fixed shortly in paraformaldehyde at 4 deg C. After this a short nuclear staining was performed with Methylgreen (FIGS. 18B and 18E; Vector Laboratories) or Hematoxylin QS (FIGS. 18C and 18F; Vector Laboratories) or the sections were kept in an aqueous milieu during the staining procedure (FIGS. 18A and 18D; unstained sections). This was followed by the dehydration procedure for LCM as proposed by Arcturus. Paraffin sections prepared according to the current invention were deparaffinized and subsequently stained and dehydrated in an identical way as the cryosections. RNA extraction procedures were performed as described in Example 9. Total RNA profiles and RIN data (Table 2) demonstrated that the Methylgreen staining was better for RNA retention and preservation of RNA quality than the hematoxylin staining as is described in literature (Okuducu A-F, Janzen V, Hahne J C, Ko Y, Wernert N: Influence of histochemical stains on quantitative gene expression after laser-assisted microdissection. Int J Mol Med 11: 449-453, 2003) and this for both cryomaterial as for tissue prepared according to the method of the invention. Indeed, the sections stained with Hematoxylin QS show a decrease of the rRNA peak height (cryosections) or a disappearance of the 28S rRNA peak (paraffin section prepared according to the current invention), while the total RNA profiles of unstained and Methylgreen stained sections were comparable. This was reflected in the RIN data, that were decreased in Hematoxylin QS stained sections and that were comparable in unstained and Methylgreen stained sections (Table 2).

TABLE 2

RIN data

|  | Cryosections | Sections prepared according to the current invention |
| --- | --- | --- |
| Unstained section | 5.4 | 3.3 |
| Methylgreen stained section | 6.7 | 3.7 |
| Hematoxylin QS stained section | 3.3 | 2.7 |

Example 15

Figure 19:
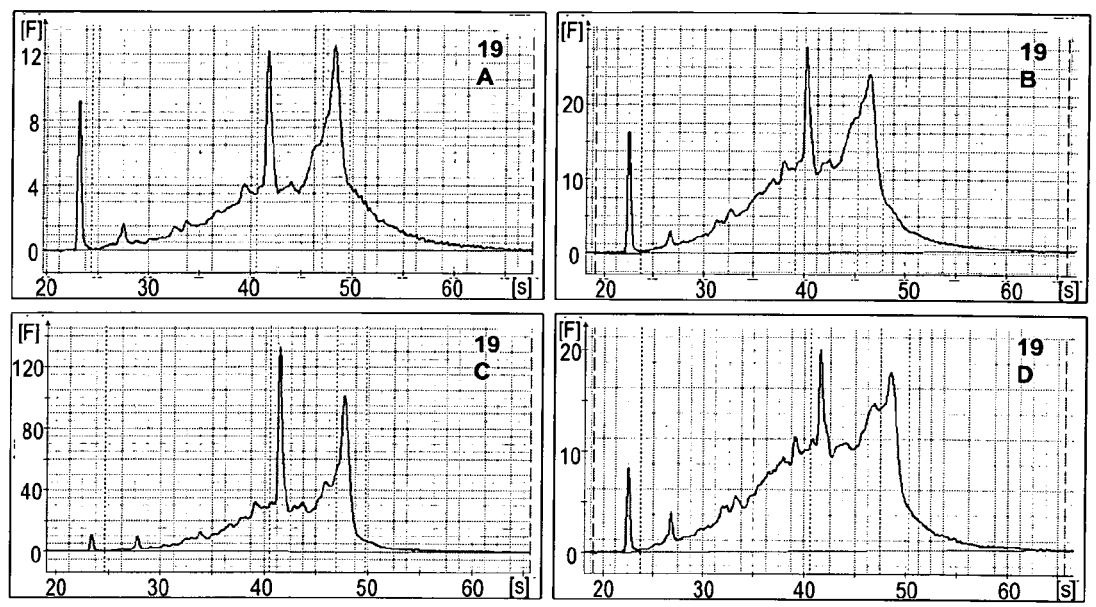
FIG. 19 shows the effect of storage of paraffin blocks prepared according to the current invention on total RNA quality. Stability of total RNA in stored FFPE blocks was compared to RNA stability in paraffin blocks prepared according to the current invention.

Stability of RNA in stored paraffin blocks, prepared according to the described invention. A systematic evaluation of the RNA stability in paraffin tissue blocks prepared according to the methods of the current invention was performed (FIG. 19). The paraffin blocks were sectioned RNase-free with disposable knives and all following procedures were performed nuclease-free. From each block two 10 µm sections were made. The sections were deparaffinized, digested with proteinase K for 3 hours followed by a precipitation step and extracted and analysed as described in Example 9. The total RNA profiles depicted in FIGS. 19A and 19B were derived from RNA extracted from the same tissue block, extracted at time 0 and after 4 months of storage at room temperature respectively. The total RNA profiles depicted in FIGS. 19C and 19D were derived from RNA extracted from the same tissue block, extracted at time 0 and after 6 months of storage at room temperature respectively. After storage, the RNA quality is still good (clearly visible rRNA peaks are still present in FIGS. 19B and 19D). Storage at room temperature induced limited degradation of the RNA inside the paraffin blocks prepared according to the current invention as can be concluded from the slightly decreased RIN numbers (respectively for FIGS. 19A, 19B, 19C and 19D are 7.4; 6.9; 6.4 and 3.7).

Example 16

Macroarray analysis of breast tumor tissues processed according to the method of the current invention.

Figure 20:
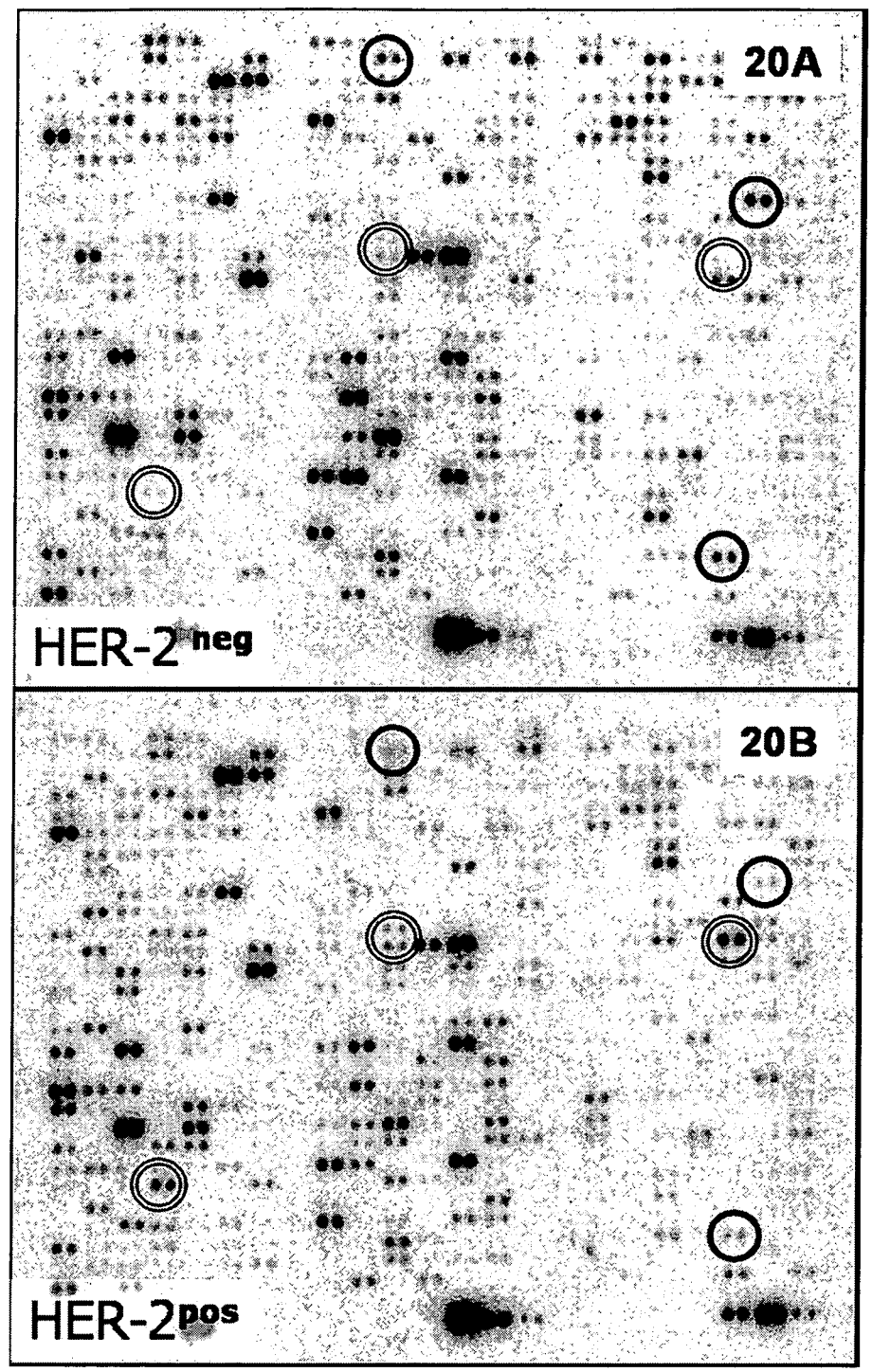
FIG. 20 shows the hybridized and developed nylon membranes of a macroarray analysis performed on RNA extracted from breast tumour tissue processed according to the current invention.

RNA was extracted from laser microdissected cells, isolated from breast tumors processed according to the current invention and analyzed on a nylon membrane macroarray. With this technique, the expression profile of approximately 600 genes, involved in apoptosis and cell cycle, could be studied. The results are shown in FIG. 20. The top membrane (FIG. 20A) shows the array of an HER-2 negative tumor and the bottom membrane (FIG. 20B) shows the array of an HER-2 positive tumor. Genes that were down-regulated (single bold circles) in the HER-2 positive sample were: G1/S-specific cyclin D1, cyclin PRAD1 and Bcl-1 oncogen. Examples of genes that were up-regulated (double circles) in the HER-2 positive sample were: ubiquitin, ezrin (cytovillin, villin 2), C-erbB2 receptor protein tyrosin kinase (HER-2).

What is claimed is:
1. A kit comprising:
 a) an FDC solution comprising, v/v:
  0.2 to 10% formaldehyde 40% w/v,
  30 to 90% methanol, and
  5 to 25% diethylether, and
  0 to 10% acetic acid (v/v).
2. The kit according to claim 1, further comprising
 b) a dehydrating-clearing solution.
3. The kit according to claim 1, further comprising
 c) an inert specimen matrix, ISM, for infiltrating the tissue samples.
4. The kit according to claim 3, wherein said ISM is low-melting paraffin suitable for impregnating the tissue at a temperature between 45 and 56 deg C.
5. The kit according to claim 1, wherein a), b) and c) are each in separate containers for separate and/or sequential application to the sample.
6. The kit according to claim 1, further comprising a crosslinking indicator system to indicate the degree of fixation.

7. The kit according to claim 1, wherein said acetic acid is at a concentration between 0.1% and 10% (v/v).

8. The kit according to claim 1, wherein the FDC solution consists of, v/v, 10% formaldehyde 40% w/v, 65% methanol, 20% diethylether and 5% acetic acid (v/v).

9. The kit according to claim 1, for processing tissue sample containing fixation-sensitive phosphoprotein.

10. The kit according to claim 1, for processing tissue sample containing fixation-sensitive DNA and/or RNA.

* * * * *

UNITED STATES PATENT AND TRADEMARK OFFICE
CERTIFICATE OF CORRECTION

PATENT NO. : 8,703,440 B2  Page 1 of 1
APPLICATION NO. : 11/997306
DATED : April 22, 2014
INVENTOR(S) : Duymelinck et al.

It is certified that error appears in the above-identified patent and that said Letters Patent is hereby corrected as shown below:

In the Specification

In column 2 at line 56, Change "-240)" to -- -240).--.

In column 6 at line 48, Change "deg C.," to --deg C.--.

In column 9 at line 21, Change "falsh-frozen" to --flash-frozen--.

In column 16 at line 36, Change "standarisations" to --standardisations--.

In column 17 at line 43, Change "(85,86)" to --(85,86).--.

In column 22 at line 28 (approx.), Change "Phloxin Saffranin" to --Phloxine Safranin--.

In column 25 at line 32, Change "nerons" to --neurons--.

In column 28 at line 43, Change "(FIG. 7C)." to --(FIG. 17 C).--.

In column 28 at line 50, Change "amplication" to --amplification--.

In column 29 at lines 14-15 (approx.), Change "heterogenous" to --heterogeneous--.

In column 29 at lines 17-18 (approx.), Change "microdissectie" to --microdissection--.

In column 30 at line 42, Change "oncogen." to --oncogene.--.

In column 30 at line 45, Change "tyrosin kinase" to --tyrosine kinase--.

Signed and Sealed this
Twenty-first Day of October, 2014

Michelle K. Lee
*Deputy Director of the United States Patent and Trademark Office*